(12) United States Patent
Songer et al.

(10) Patent No.: US 7,445,626 B2
(45) Date of Patent: Nov. 4, 2008

(54) DEVICE AND METHOD FOR SUTURING TISSUE

(75) Inventors: Ronald W. Songer, San Jose, CA (US); James W. Vetter, Portola Valley, CA (US); Enrique J. Klein, Los Altos, CA (US); Bernard A. Andreas, Redwood City, CA (US); Michael Barrett, Campbell, CA (US); Mark J. Foley, Las Gatos, CA (US); Brian Gore, Orlando, FL (US); Lewis Isbell, Union City, CA (US); T. Daniel Gross, Los Gatos, CA (US); Tomoaki Hinohara, Portola Valley, CA (US)

(73) Assignee: Abbott Laboratories, Abbott Park, IL (US)

( * ) Notice: Subject to any disclaimer, the term of this patent is extended or adjusted under 35 U.S.C. 154(b) by 301 days.

(21) Appl. No.: 10/737,668

(22) Filed: Dec. 16, 2003

(65) Prior Publication Data

US 2005/0171561 A1 Aug. 4, 2005

Related U.S. Application Data

(60) Continuation of application No. 10/033,689, filed on Dec. 28, 2001, now abandoned, which is a continuation of application No. 08/883,246, filed on Jun. 26, 1997, now Pat. No. 6,355,050, which is a continuation-in-part of application No. 08/824,031, filed on Mar. 26, 1997, now Pat. No. 6,036,699, which is a continuation-in-part of application No. 08/259,410, filed on Jun. 14, 1994, now Pat. No. 5,779,719, which is a division of application No. 07/989,611, and a continuation-in-part of application No. 07/989,611, filed on Dec. 10, 1992, now Pat. No. 5,417,699.

(51) Int. Cl.
A61B 17/06 (2006.01)
(52) U.S. Cl. ...................................... 606/224
(58) Field of Classification Search ................. 606/148, 606/139, 144, 213, 167, 170, 185, 222, 223, 606/224, 228, 230, 232; 623/1.36; 112/224, 112/225, 171; 132/321; 223/99
See application file for complete search history.

(56) References Cited

U.S. PATENT DOCUMENTS 312,408 A 2/1885 Wackerhagen (Continued)

FOREIGN PATENT DOCUMENTS

DE 4210724 C1 7/1993

(Continued)

OTHER PUBLICATIONS

US 5,820,544, 06/1974, Semm (withdrawn).

(Continued)

Primary Examiner—Todd E. Manahan
Assistant Examiner—Christina D Gettman
(74) Attorney, Agent, or Firm—Workman Nydegger

(57) ABSTRACT

Systems for suturing a tissue layer having two sides with a suture be releasably retaining at least a portion of the suture in a stationary position on one side of the tissue layer. The portion of the suture is retrieved through the tissue layer from the opposite side whereby the suture is drawn from one side to the opposite side. Systems for suturing the wall of a tubular graft having two sides is also provided using a suture by releasably retaining at least a portion of the suture on one side of the wall. the portion of the length of suture is retrieved through the wall of the graft to the opposite side of the wall.

13 Claims, 20 Drawing Sheets

U.S. PATENT DOCUMENTS

| | | |
|---|---|---|
| 597,165 A | 1/1898 | Hall |
| 659,422 A | 10/1900 | Shidler |
| 989,231 A | 4/1911 | Davis |
| 1,625,602 A | 4/1927 | Gould et al. |
| 2,127,903 A | 8/1938 | Bowen |
| 2,397,823 A | 4/1946 | Walter |
| 2,588,589 A | 3/1952 | Tauber |
| 2,646,045 A | 7/1953 | Priestley |
| 2,692,599 A | 10/1954 | Creelman |
| 2,959,172 A | 11/1960 | Held |
| 3,033,156 A | 5/1962 | Verlish |
| 3,104,666 A | 9/1963 | Hale et al. |
| 3,470,875 A | 10/1969 | Johnson |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,820,544 A | 6/1974 | Semm |
| 3,918,455 A * | 11/1975 | Coplan ................... 606/225 |
| 3,926,194 A | 12/1975 | Greenberg et al. |
| 3,939,820 A | 2/1976 | Grayzel |
| 4,018,228 A | 4/1977 | Goosen |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,492,229 A | 1/1985 | Grunwald |
| 4,493,323 A | 1/1985 | Albright et al. |
| 4,553,543 A | 11/1985 | Amarasinghe |
| 4,586,614 A | 5/1986 | Ger |
| 4,587,969 A | 5/1986 | Gillis |
| 4,596,559 A | 6/1986 | Fleischhacker |
| 4,629,450 A | 12/1986 | Suzuki et al. |
| 4,651,733 A | 3/1987 | Mobin-Uddin |
| 4,702,250 A | 10/1987 | Ovil et al. |
| 4,723,549 A | 2/1988 | Wholey et al. |
| 4,738,666 A | 4/1988 | Fuqua |
| 4,744,364 A | 5/1988 | Kensey |
| 4,803,984 A | 2/1989 | Narayanan et al. |
| 4,836,205 A | 6/1989 | Barrett |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,926,860 A | 5/1990 | Stice et al. |
| 4,929,246 A | 5/1990 | Sinofsky |
| 4,935,027 A | 6/1990 | Yoon |
| 4,957,498 A | 9/1990 | Caspari et al. |
| 4,966,600 A | 10/1990 | Songer et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,047,039 A | 9/1991 | Avant et al. |
| 5,059,201 A | 10/1991 | Asnis |
| 5,061,274 A | 10/1991 | Kensey |
| 5,078,721 A | 1/1992 | McKeating |
| 5,080,664 A | 1/1992 | Jain |
| 5,100,419 A | 3/1992 | Ehlers |
| 5,100,432 A | 3/1992 | Matsutani |
| 5,109,780 A | 5/1992 | Slouf et al. |
| 5,129,913 A | 7/1992 | Ruppert |
| 5,147,373 A | 9/1992 | Ferzli |
| 5,160,339 A | 11/1992 | Chen et al. |
| 5,171,251 A | 12/1992 | Bregen et al. |
| 5,192,294 A | 3/1993 | Blake, III |
| 5,192,301 A * | 3/1993 | Kamiya et al. ............... 606/213 |
| 5,192,302 A | 3/1993 | Kensey et al. |
| 5,207,703 A | 5/1993 | Jain |
| 5,217,470 A | 6/1993 | Weston |
| 5,219,358 A | 6/1993 | Bendel et al. |
| 5,222,974 A * | 6/1993 | Kensey et al. ............... 606/213 |
| 5,234,443 A | 8/1993 | Phan et al. |
| 5,242,427 A | 9/1993 | Bilweis |
| 5,250,033 A | 10/1993 | Evans et al. |
| 5,250,053 A | 10/1993 | Snyder |
| 5,254,126 A | 10/1993 | Filipi et al. |
| 5,258,003 A | 11/1993 | Ciaglia et al. |
| 5,279,311 A | 1/1994 | Snyder |
| 5,281,236 A * | 1/1994 | Bagnato et al. ............. 606/139 |
| 5,281,237 A * | 1/1994 | Gimpelson ................ 606/144 |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,292,309 A | 3/1994 | VanTassel et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A * | 4/1994 | Hathaway et al. ........... 606/144 |
| 5,304,185 A | 4/1994 | Taylor |
| 5,306,254 A | 4/1994 | Nash et al. |
| 5,312,024 A | 5/1994 | Grant et al. |
| 5,320,632 A | 6/1994 | Heidmueller |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,354,312 A | 10/1994 | Brinkerhoff et al. |
| 5,364,407 A | 11/1994 | Poll |
| 5,364,408 A | 11/1994 | Gordon |
| 5,368,595 A * | 11/1994 | Lewis ........................ 606/72 |
| 5,368,601 A | 11/1994 | Sauer et al. |
| 5,374,275 A | 12/1994 | Bradley et al. |
| 5,376,096 A | 12/1994 | Foster |
| 5,383,896 A | 1/1995 | Gershony et al. |
| 5,385,569 A | 1/1995 | Swor |
| 5,387,221 A | 2/1995 | Bisgaard |
| 5,387,227 A | 2/1995 | Grice |
| 5,395,332 A | 3/1995 | Ressemann et al. |
| 5,395,349 A | 3/1995 | Quiachon et al. |
| 5,397,310 A * | 3/1995 | Chu et al. ................... 604/158 |
| 5,397,325 A | 3/1995 | Della Badia et al. |
| 5,403,329 A | 4/1995 | Hinchcliffe |
| 5,403,331 A | 4/1995 | Chesterfield et al. |
| 5,403,338 A | 4/1995 | Milo |
| 5,411,481 A | 5/1995 | Allen et al. |
| 5,413,571 A | 5/1995 | Katsaros et al. |
| 5,417,699 A | 5/1995 | Klein et al. |
| 5,425,705 A | 6/1995 | Evard et al. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schob et al. |
| 5,454,834 A | 10/1995 | Boebel et al. |
| 5,458,574 A | 10/1995 | Machold et al. |
| 5,464,426 A | 11/1995 | Bonutti |
| 5,470,338 A | 11/1995 | Whitfield et al. |
| 5,476,469 A | 12/1995 | Hathaway et al. |
| 5,476,470 A | 12/1995 | Fitzgibbons, Jr. |
| 5,478,309 A | 12/1995 | Sweezer et al. |

| | | | | | | |
|---|---|---|---|---|---|---|
| 5,478,353 | A | 12/1995 | Yoon | 5,876,411 A | 3/1999 | Kontos |
| 5,480,407 | A | 1/1996 | Wan et al. | 5,902,311 A | 5/1999 | Andreas et al. |
| 5,486,190 | A | 1/1996 | Green | 5,904,597 A | 5/1999 | Doi et al. |
| 5,489,295 | A | 2/1996 | Piplani et al. | 5,904,690 A | 5/1999 | Middleman et al. |
| 5,496,332 | A | 3/1996 | Sierra et al. | 5,904,697 A | 5/1999 | Gifford, III et al. |
| 5,507,744 | A | 4/1996 | Tay et al. | 5,928,266 A | 7/1999 | Kontos |
| 5,507,755 | A | 4/1996 | Gresl et al. | 5,951,590 A | 9/1999 | Goldfarb |
| 5,507,757 | A | 4/1996 | Sauer et al. | 5,954,732 A | 9/1999 | Hart et al. |
| 5,507,758 | A | 4/1996 | Thomason et al. | 5,972,030 A | 10/1999 | Garrison et al. |
| 5,509,902 | A | 4/1996 | Raulerson | 5,980,539 A | 11/1999 | Kontos |
| 5,520,655 | A | 5/1996 | Davila et al. | 5,997,555 A | 12/1999 | Kontos |
| 5,520,665 | A | 5/1996 | Fleetwood | 6,001,109 A | 12/1999 | Kontos |
| 5,520,702 | A | 5/1996 | Sauer et al. | 6,024,747 A | 2/2000 | Kontos |
| 5,527,321 | A | 6/1996 | Hinchliffe | 6,036,699 A | 3/2000 | Andreas et al. |
| 5,527,322 | A | 6/1996 | Klein et al. | 6,048,351 A | 4/2000 | Gordon et al. |
| D372,310 | S | 7/1996 | Hartnett | 6,048,357 A | 4/2000 | Kontos |
| 5,531,700 | A | 7/1996 | Moore et al. | 6,077,276 A | 6/2000 | Kontos |
| 5,540,701 | A | 7/1996 | Sharkey et al. | 6,077,279 A | 6/2000 | Kontos |
| 5,540,704 | A | 7/1996 | Gordon et al. | 6,117,144 A | 9/2000 | Nobles et al. |
| 5,545,171 | A | 8/1996 | Sharkey et al. | 6,132,439 A | 10/2000 | Kontos |
| 5,545,178 | A | 8/1996 | Kensey et al. | 6,136,010 A | 10/2000 | Modesitt et al. |
| 5,545,180 | A | 8/1996 | Le et al. | 6,139,556 A | 10/2000 | Kontos |
| 5,549,618 | A | 8/1996 | Fleenor et al. | 6,190,396 B1 | 2/2001 | Whitin et al. |
| 5,549,631 | A | 8/1996 | Bonutti | 6,206,893 B1 | 3/2001 | Klein et al. |
| 5,554,162 | A | 9/1996 | DeLange | 6,355,050 B1 | 3/2002 | Andreas et al. |
| 5,562,686 | A | 10/1996 | Sauer et al. | 6,358,258 B1 | 3/2002 | Arcia et al. |
| 5,562,688 | A | 10/1996 | Riza | 6,428,549 B1 | 8/2002 | Kontos |
| 5,562,728 | A | 10/1996 | Lazarus et al. | 6,436,109 B1 | 8/2002 | Kontos |
| 5,567,435 | A * | 10/1996 | Hubbell et al. .............. 424/426 | 6,451,031 B1 | 9/2002 | Kontos |
| 5,569,269 | A * | 10/1996 | Hart et al. ................... 606/144 | 6,517,553 B2 | 2/2003 | Klein et al. |
| 5,569,271 | A | 10/1996 | Hoel | 6,558,399 B1 | 5/2003 | Isbell et al. |
| 5,573,540 | A | 11/1996 | Yoon | 6,641,592 B1 | 11/2003 | Saur et al. |
| 5,591,179 | A | 1/1997 | Edelstein | 7,029,480 B2 | 4/2006 | Klein et al. |
| 5,591,206 | A | 1/1997 | Moufarrege | 7,029,481 B1 | 4/2006 | Burdulis, Jr. et al. |
| 5,593,421 | A | 1/1997 | Bauer | 7,048,747 B2 | 5/2006 | Arcia et al. |
| 5,603,718 | A | 2/1997 | Xu | 7,179,266 B2 | 2/2007 | Kontos |
| 5,607,435 | A * | 3/1997 | Sachdeva et al. ............ 606/139 | 2002/0095164 A1 | 7/2002 | Andreas |
| 5,611,794 | A | 3/1997 | Sauer et al. | 2003/0093093 A1 | 5/2003 | Modesitt et al. |
| 5,613,974 | A * | 3/1997 | Andreas et al. ............. 606/144 | 2004/0097978 A1 | 5/2004 | Modesitt et al. |
| 5,613,975 | A | 3/1997 | Christy | 2004/0186487 A1 | 9/2004 | Klein |
| 5,643,289 | A | 7/1997 | Sauer et al. | 2004/0210251 A1 | 10/2004 | Kontos |
| 5,669,917 | A | 9/1997 | Sauer et al. | 2005/0149065 A1 | 7/2005 | Modesitt et al. |
| 5,700,273 | A | 12/1997 | Buelna et al. | 2006/0167476 A1 | 7/2006 | Burdulis |
| 5,713,910 | A | 2/1998 | Gordon et al. | 2006/0167477 A1 | 7/2006 | Arcia |
| 5,716,369 | A | 2/1998 | Riza | 2006/0173469 A1 | 8/2006 | Klein |
| 5,720,574 | A | 2/1998 | Barella | | | |
| 5,720,757 | A | 2/1998 | Hathaway et al. | FOREIGN PATENT DOCUMENTS | | |
| 5,728,133 | A | 3/1998 | Kontos | DE | 9217932 U1 | 7/1993 |
| 5,728,151 | A | 3/1998 | Garrison et al. | EP | 0 140 557 | 5/1985 |
| 5,741,276 | A | 4/1998 | Poloyko et al. | EP | 0 207 545 | 1/1987 |
| 5,741,280 | A | 4/1998 | Fleenor | EP | 0 474 887 | 3/1992 |
| 5,755,727 | A | 5/1998 | Kontos | EP | 0 478 358 | 4/1992 |
| 5,759,188 | A | 6/1998 | Yoon | EP | 0478 887 | 4/1992 |
| 5,766,183 | A | 6/1998 | Sauer | EP | 0 589 409 | 9/1992 |
| 5,766,186 | A | 6/1998 | Faraz et al. | EP | 0 624 343 | 4/1993 |
| 5,779,719 | A | 7/1998 | Klein et al. | EP | 0 542 126 | 5/1993 |
| 5,792,151 | A | 8/1998 | Heck et al. | EP | 0 568 098 | 11/1993 |
| 5,792,152 | A | 8/1998 | Klein et al. | EP | 0 669 101 | 8/1995 |
| 5,799,661 | A | 9/1998 | Boyd et al. | EP | 0 669 102 | 8/1995 |
| 5,810,849 | A | 9/1998 | Kontos | EP | 0 669 103 | 8/1995 |
| 5,810,850 | A | 9/1998 | Hathaway et al. | EP | 684012 A2 * | 11/1995 |
| 5,817,113 | A | 10/1998 | Gifford, III et al. | EP | 0 812 571 | 12/1997 |
| 5,820,631 | A | 10/1998 | Nobles | EP | 01407557 A | 1/2003 |
| 5,824,010 | A | 10/1998 | McDonald | FR | 1059544 | 3/1954 |
| 5,824,111 | A | 10/1998 | Schall et al. | JP | 2119866 A | 5/1990 |
| 5,830,125 | A | 11/1998 | Scribner et al. | JP | 542161 A | 2/1993 |
| 5,836,955 | A | 11/1998 | Buelna et al. | SU | 820810 | 4/1981 |
| 5,836,956 | A | 11/1998 | Buelna et al. | SU | 993922 | 2/1983 |
| 5,846,253 | A | 12/1998 | Buelna et al. | SU | 1093329 | 5/1984 |
| 5,848,714 | A | 12/1998 | Robson et al. | SU | 1174036 | 8/1985 |
| 5,855,585 | A | 1/1999 | Kontos | SU | 1544383 | 2/1990 |
| 5,860,990 | A | 1/1999 | Nobles et al. | SU | 1648400 | 5/1991 |
| 5,860,991 | A | 1/1999 | Klein et al. | | | |

| | | |
|---|---|---|
| WO | WO 85/03858 | 9/1985 |
| WO | WO 94/05213 | 3/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/35065 | 12/1995 |
| WO | WO 97/03613 | 2/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 98/04195 | 2/1998 |
| WO | WO 98/42262 | 10/1998 |
| WO | WO 00/12013 | 3/2000 |
| WO | WO 00/51498 | 9/2000 |
| WO | WO 01/19259 | 3/2001 |
| WO | WO 02/36021 | 5/2002 |
| WO | WO 2005/065549 | 7/2005 |

OTHER PUBLICATIONS

U.S. Appl. No. 09/608,832, filed Jun. 30, 2000, Burdulis.
U.S. Appl. No. 09/610,564, filed Jun. 30, 2000, Burdulis.
Cardiac Catheterization and Angiography, 3rd Ed., Lea & Febiger, Philadelphia, 1986.
Cardio-Thoracic Systems Prospectus dated Mar. 20, 1996.
Datascope Corporation, Montvale, NJ (1991) 1 PG, American Heart Assoc. Meeting, Anaheim.
Elgiloy Brochure, Jun. 23, 1959, Elgin National Watch Co., Elgin, IL.
Elgin National Watch Company, Product Brochure entitled "Elgiloy, A Cobalt Nickel Spring Alloy", 33 pages.
Faulkner, Catherine B., Letter regarding "VasoSeal Vascular Hemostasis", *Datascope*, New Jersey, 1 page.
Kensey Nash Corporation, Exton, PA, "The Hemostatic Puncture Closure Device", 2 pages.
Laurus Medical Corporation, "Endoscopic Suturing Made Simple", The Laurus ND-2600 Needle Driver, Irvine, CA. 1 page.
Product Brochure "The Prove Solution to Endoscopic Suturing", Laurus Medical Corp., Irvine, CA. Oct. 1994.
Rema-Medizintechnik GmbH, Product Brochure entitled "REMA", 7 pages.
Product Brochure "SuperStitch-Closure Made SimpleTM", Sutura, Inc.
The Laurus In-Line Endoscopic Suturing Device (Oct. 1994) 1 page.
5,417,699, Office Action, May 12, 1993.
5,417,699, Office Action, Aug. 1, 1994.
5,417,699, Notice of Allowance, Nov. 3, 1994.
5,417,699 Issue Notification, Apr. 17, 1995.
5,527,322, Office Action, Sep. 16, 1994.
5,527,322, Office Action, May 30, 1995.
5,527,322, Office Action, Oct. 26, 1995.
5,527,322, Notice of Allowance, Dec. 15, 1995.
5,527,322, Issue Notification, May 13, 1996.
5,613,974, Office Action, Jun. 5, 1995.
5,613,974, Office Action, Jan. 5, 1996.
5,613,974, Notice of Allowance, May 22, 1996.
5,613,974, Issue Notification, Feb. 18, 1997.
5,779,719, Office Action, Jun. 1, 1995.
5,779,719, Notice of Allowance, Feb. 6, 1998.
5,779,719, Issue Notification, Jun. 8, 1998.
5,792,152, Office Action, Jan. 21, 1997.
5,792,152, Notice of Allowance, Oct. 17, 1997.
5,792,152, Issue Notification, Jul. 7, 1998.
6,036,699, Office Action, Sep. 14, 1998.
6,036,699, Office Action, Apr. 13, 1999.
6,036,699, Notice of Allowance, Jul. 15, 1999.
6,036,699, Issue Notification, Mar. 2, 2000.
6,206,893, Office Action, Jul. 10, 2000.
6,206,893, Notice of Allowance, Oct. 25, 2000.
6,206,893, Issue Notification, Mar. 9, 2001.
6,355,050, Office Action, Jul. 23, 1998.
6,355,050, Office Action, Oct. 13, 1999.
6,355,050, Office Action, Oct. 23, 2000.
6,355,050, Office Action, Jul. 11, 2001.
6,355,050, Notice of Allowance, Sep. 11, 2001.
6,355,050, Issue Notification, Feb. 21, 2002.
6,358,258, Office Action, Nov. 6, 2000.
6,358,258, Notice of Allowance, Apr. 20, 2001.
6,358,258, Notice of Allowance, Sep. 10, 2001.
6,358,258, Issue Notification, Mar. 1, 2002.
6,517,553, Office Action, Oct. 23, 2001.
6,517,553, Office Action, Jun. 17, 2002.
6,517,553, Notice of Allowance, Sep. 9, 2002.
6,517,553, Issue Notification, Jan. 23, 2003.
6,558,399, Office Action, Jul. 11, 2002.
6,558,399, Notice of Allowance, Dec. 24, 2002.
6,558,399, Issue Notification, Apr. 17, 2003.
7,029,480, Office Action, Mar. 17, 2005.
7,029,480, Office Action, Jun. 10, 2005.
7,029,480, Notice of Allowance, Nov. 17, 2005.
7,029,480, Issue Notification, Mar. 29, 2006.
7,029,481, Office Action, Feb. 16, 2005.
7,029,481, Office Action, Jul. 7, 2005.
7,029,481, Notice of Allowance, Nov. 15, 2005.
7,029,481, Issue Notification, Mar. 29, 2006.
7,048,747, Office Action, Mar. 17, 2004.
7,048,747, Office Action, Feb. 28, 2005.
7,048,747, Office Action, May 25, 2005.
7,048,747, Office Action, Aug. 24, 2005.
7,048,747, Office Action, Nov. 8, 2005.
7,048,747, Notice of Allowance, Dec. 13, 2005.
7,048,747, Issue Notification, May 3, 2006.
2002/0095164, Office Action, Sep. 30, 2003.
2004/0186487, Office Action, Sep. 5, 2006.
2004/0186487, Office Action, Jul. 16, 2007.
2005/0149065, Office Action, Mar. 23, 2007.
2005/0149065, Notice of Allowance, Sep. 10, 2007.
2006/0167476, Notice of Allowance, Sep. 20, 2007.
2006/0167477, Office Action, Sep. 7, 2007.

* cited by examiner

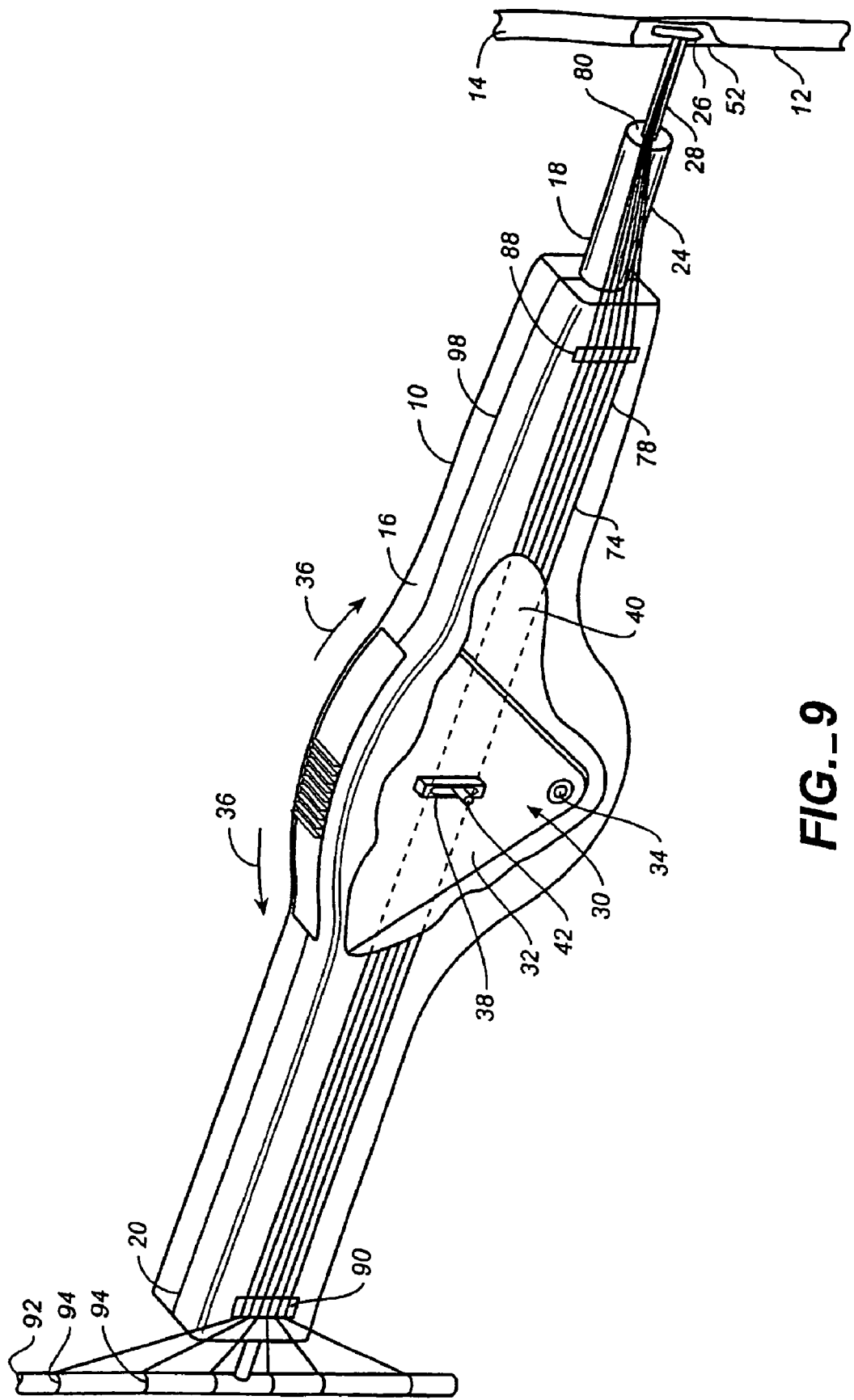
FIG._9

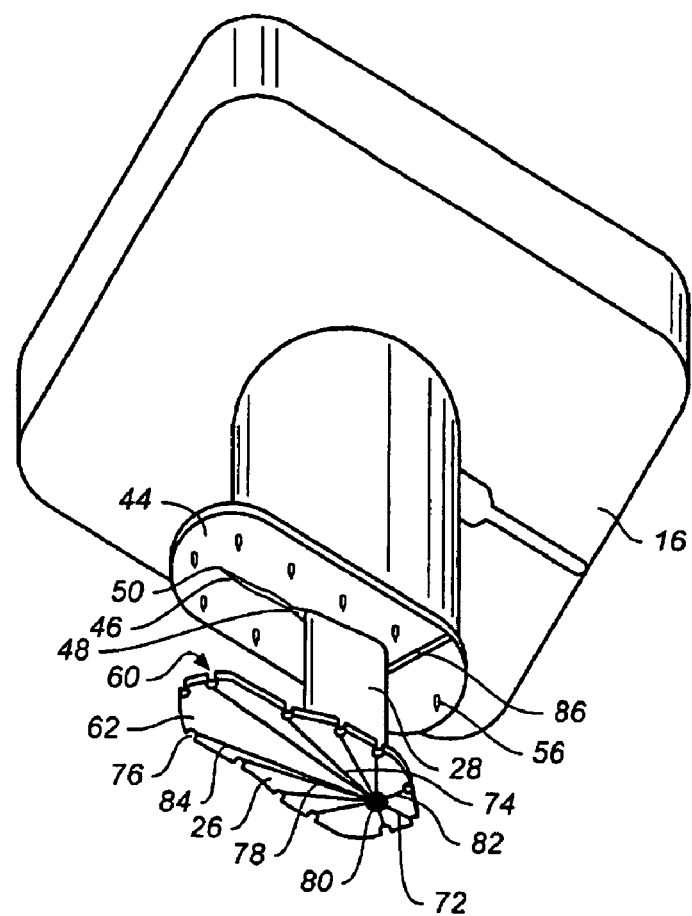
FIG._10
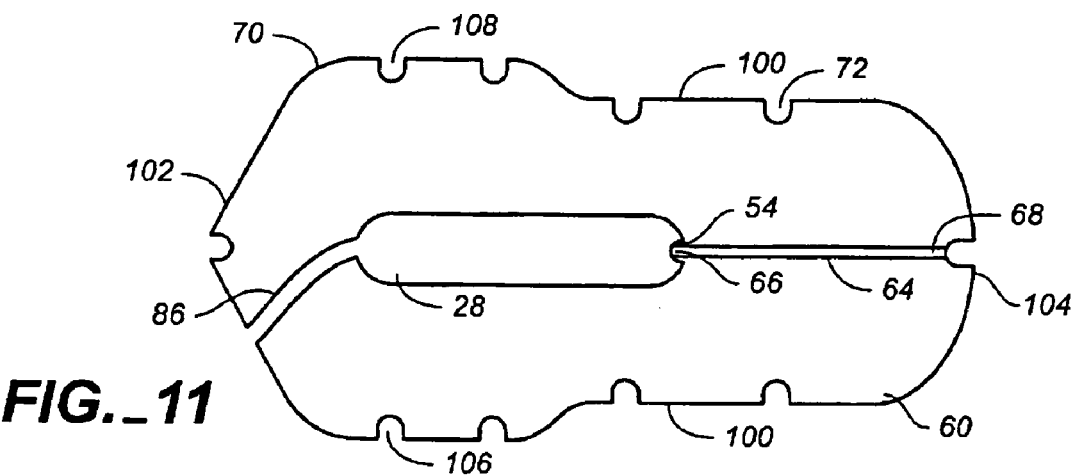
FIG._11
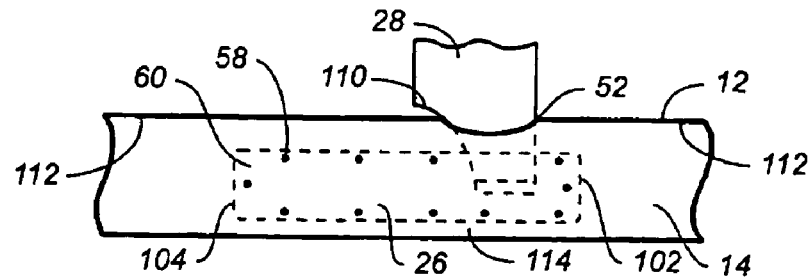
FIG._12

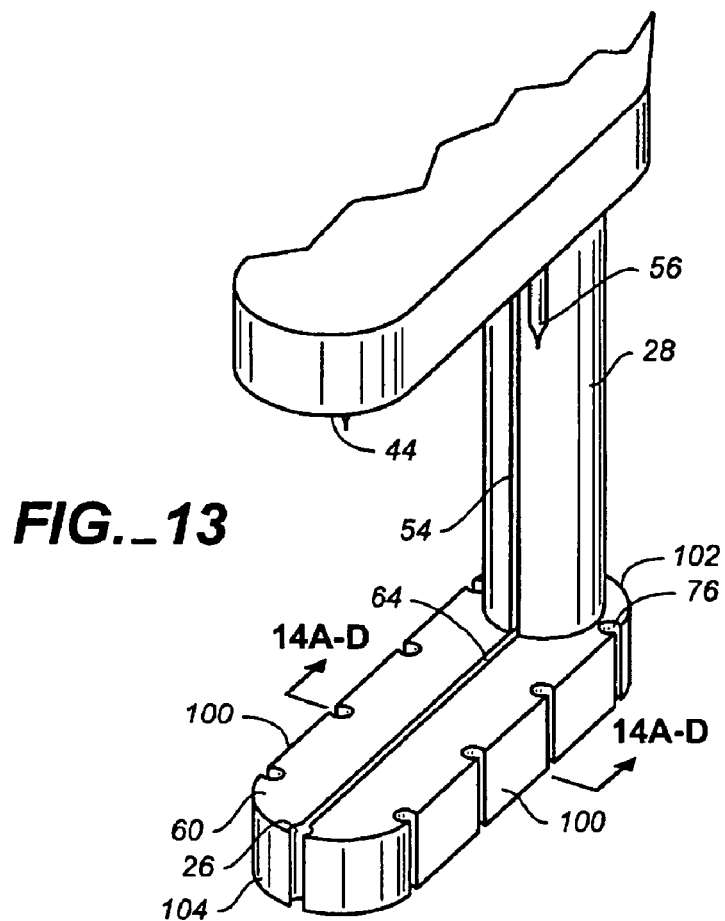
FIG._13
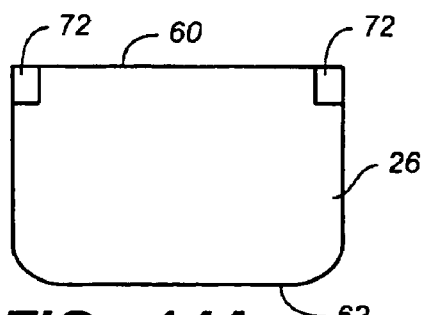
FIG._14A
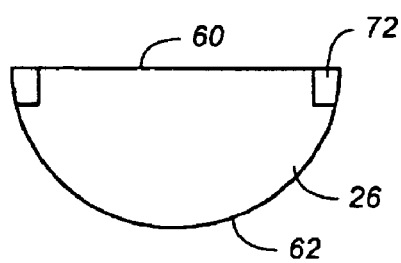
FIG._14B
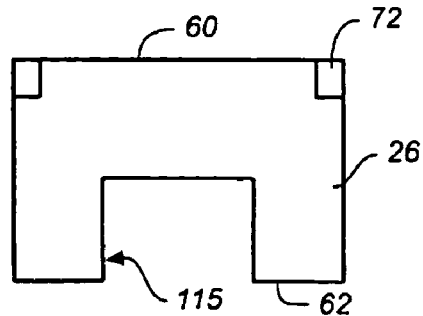
FIG._14C
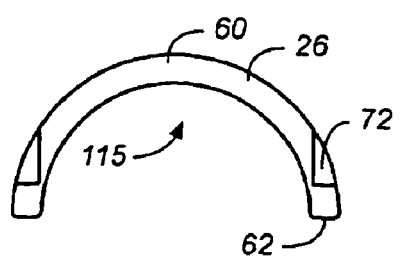
FIG._14D

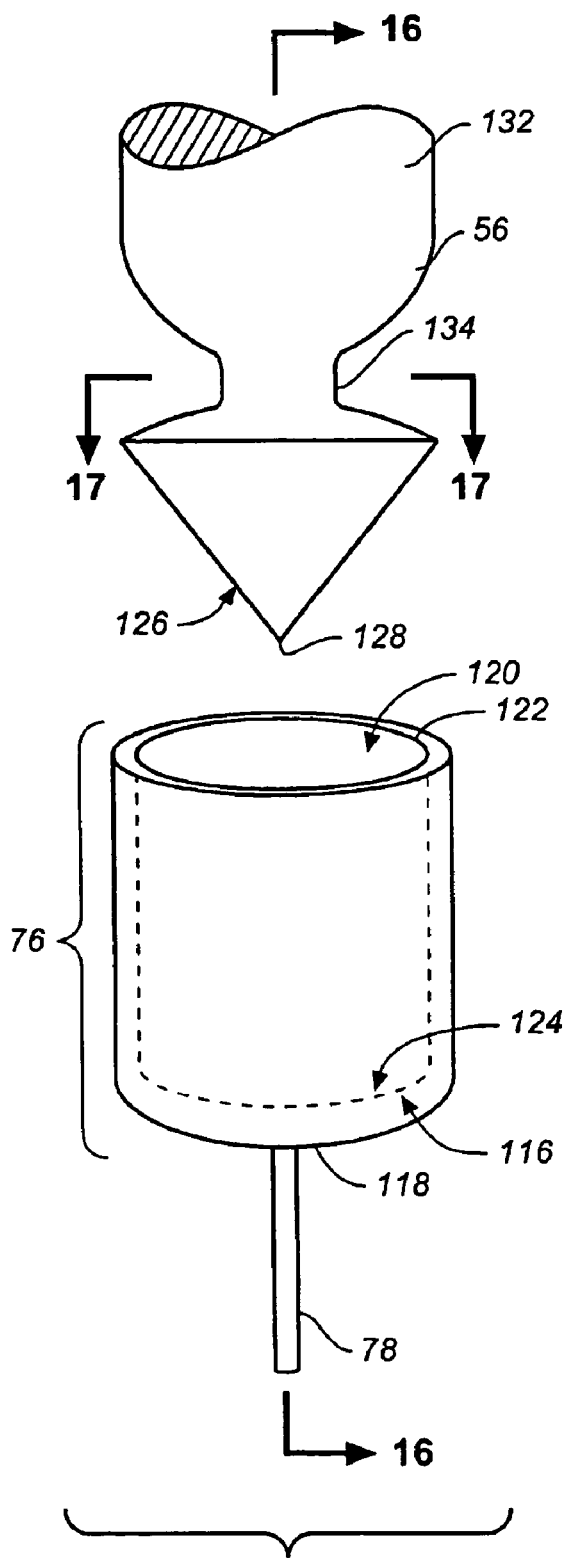
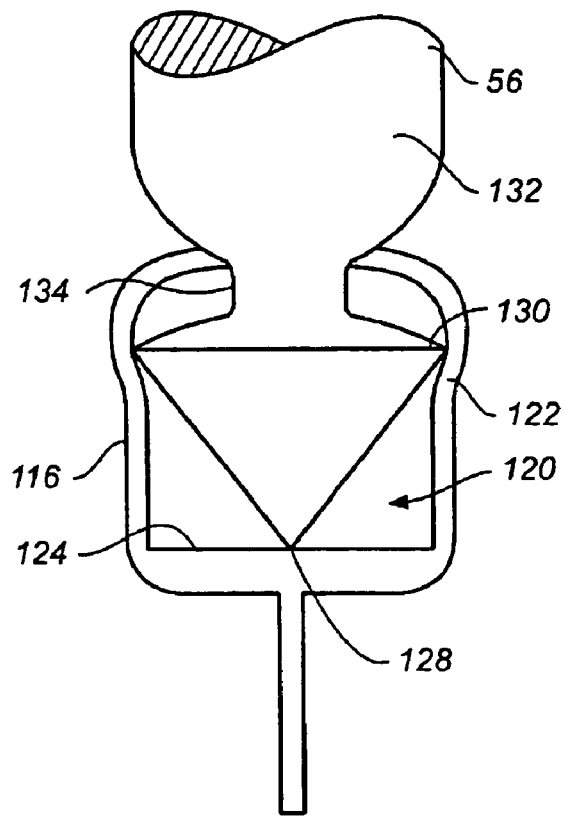
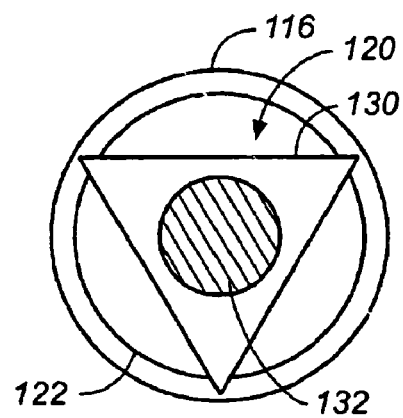
FIG._15
FIG._16
FIG._17

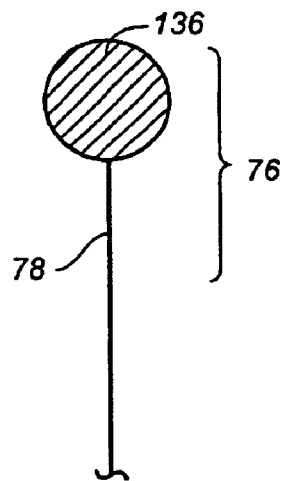
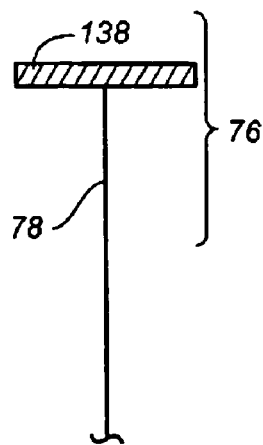
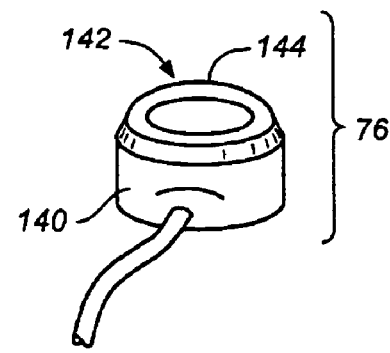
FIG._18A  FIG._18B  FIG._18C
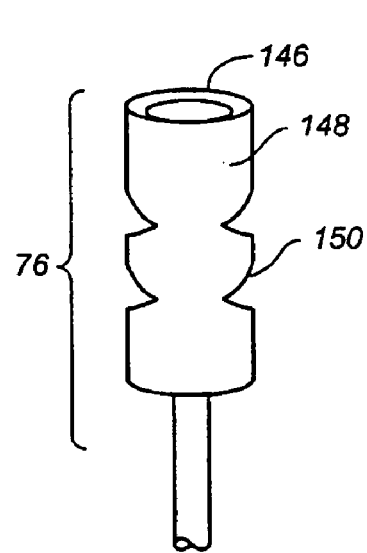
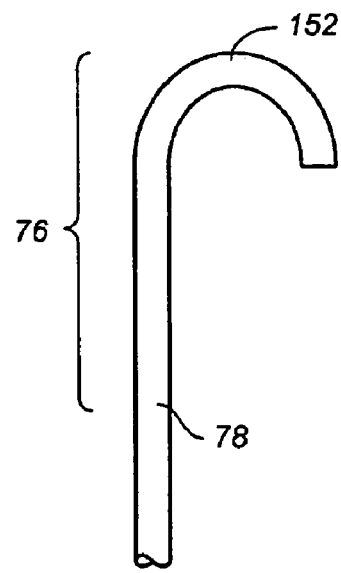
FIG._18D  FIG._18E

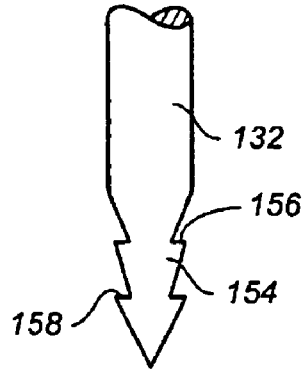
FIG._19A
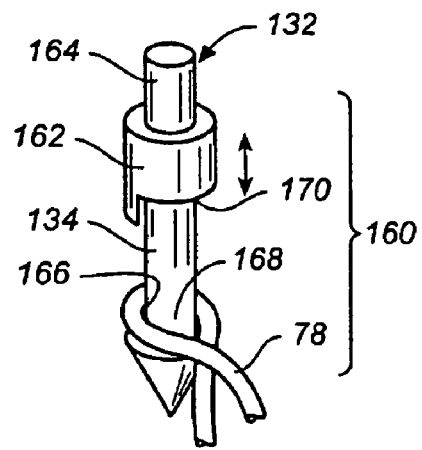
FIG._19B
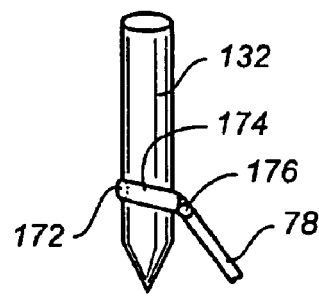
FIG._19C
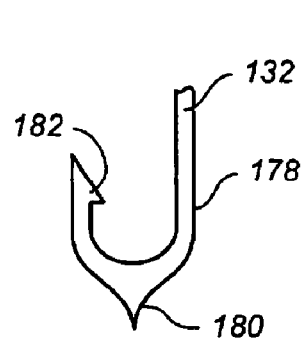
FIG._19D
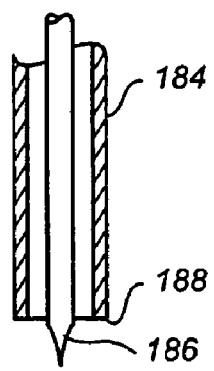
FIG._19E

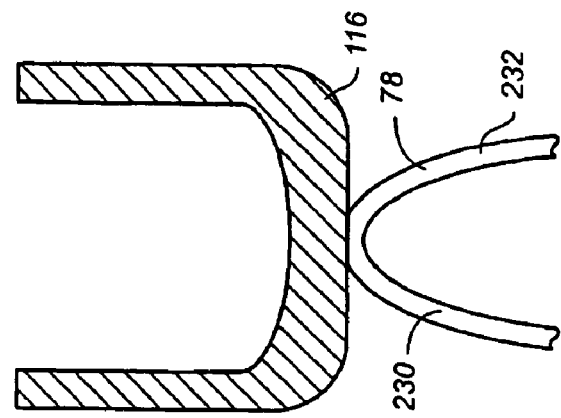
FIG._22
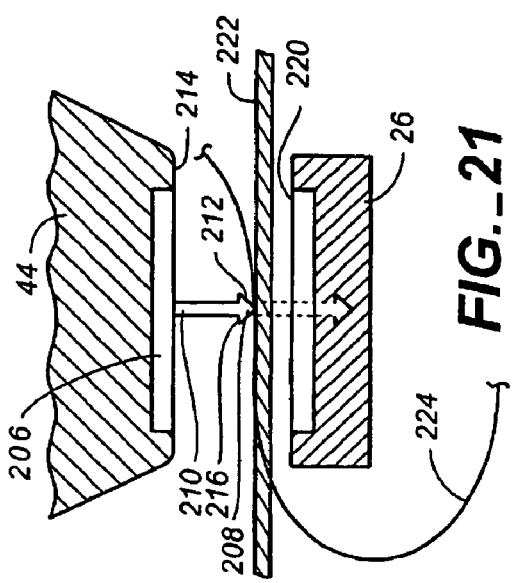
FIG._20
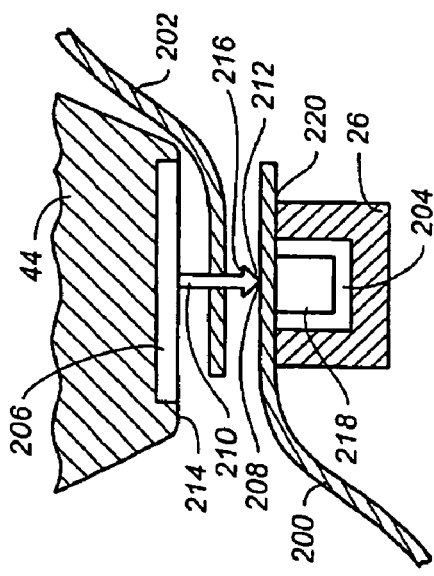
FIG._23
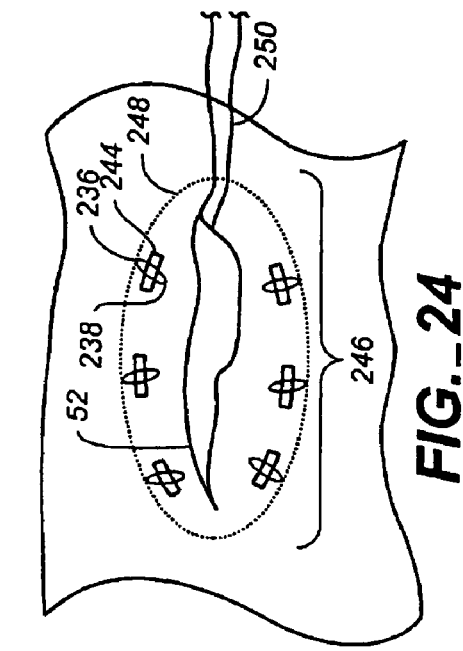
FIG._21
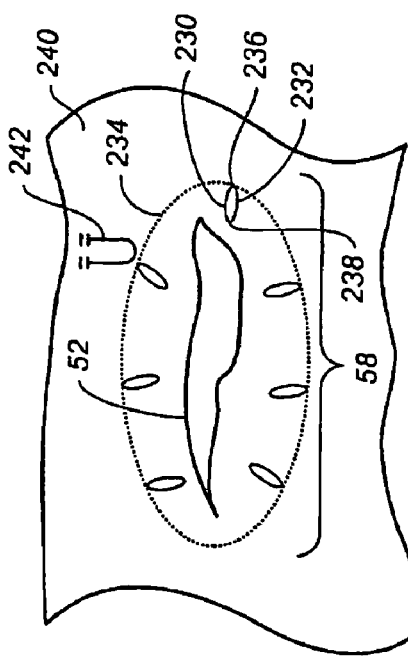
FIG._24

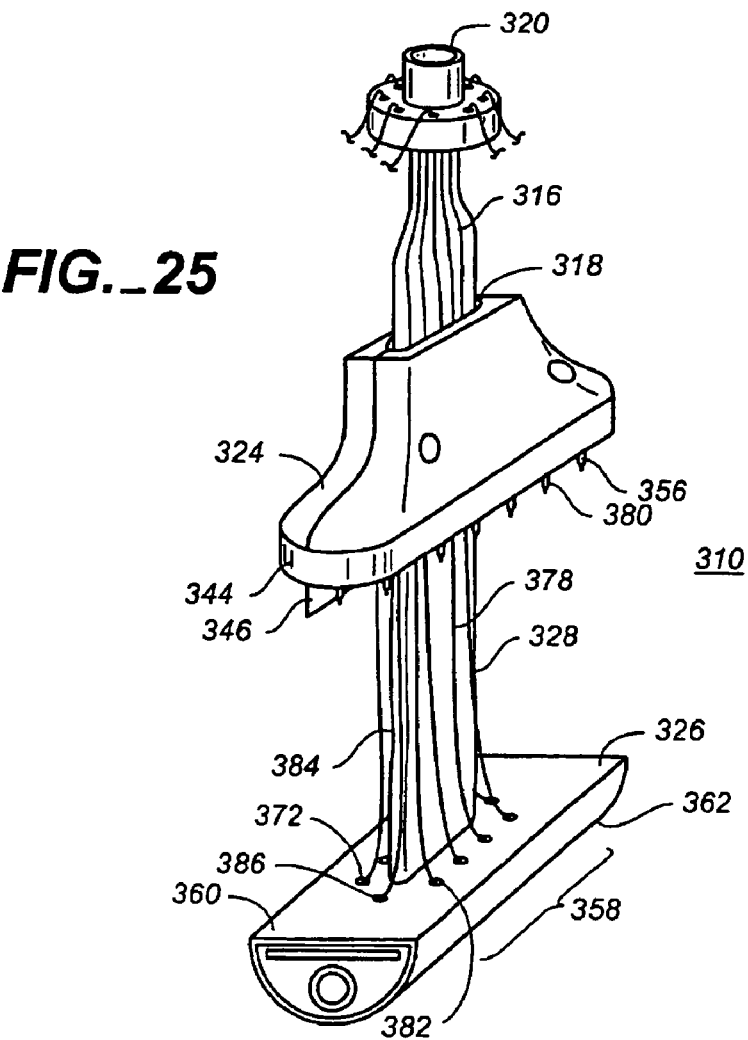
FIG._25
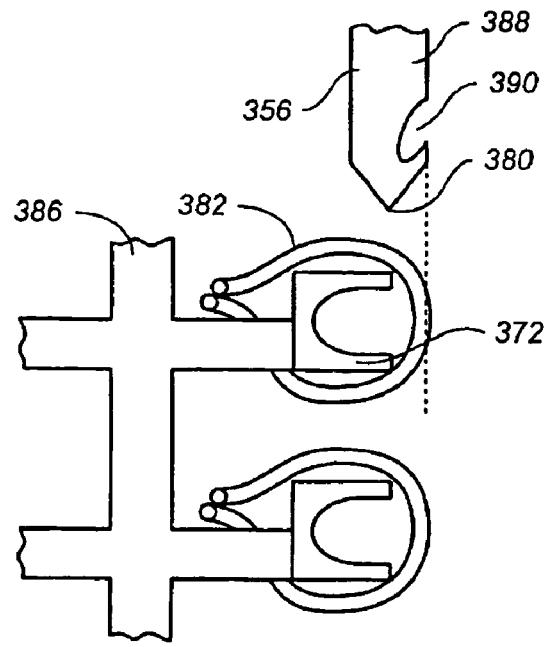
FIG._26

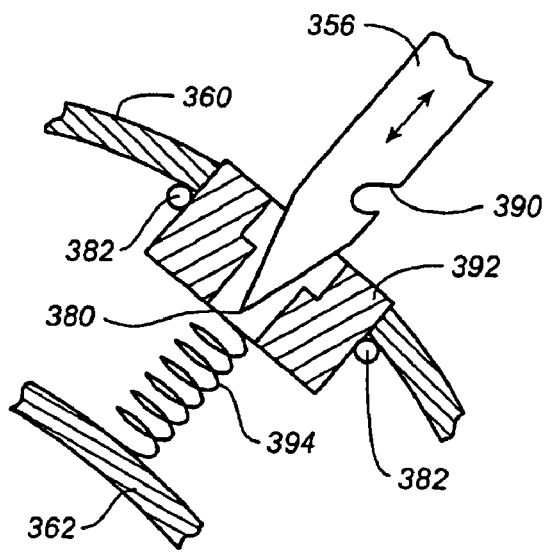
FIG._27
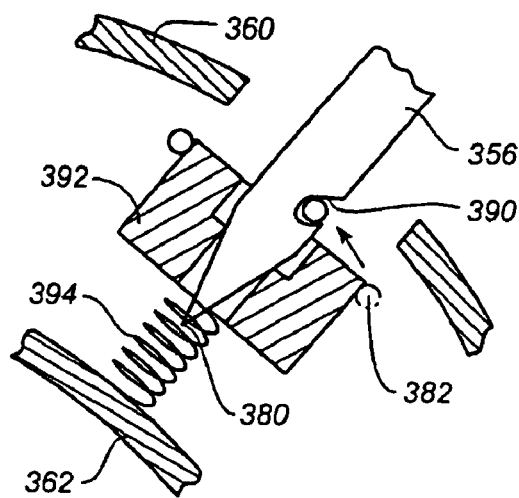
FIG._29
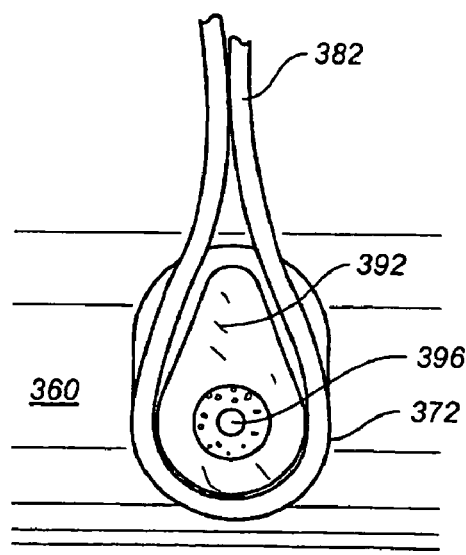
FIG._28
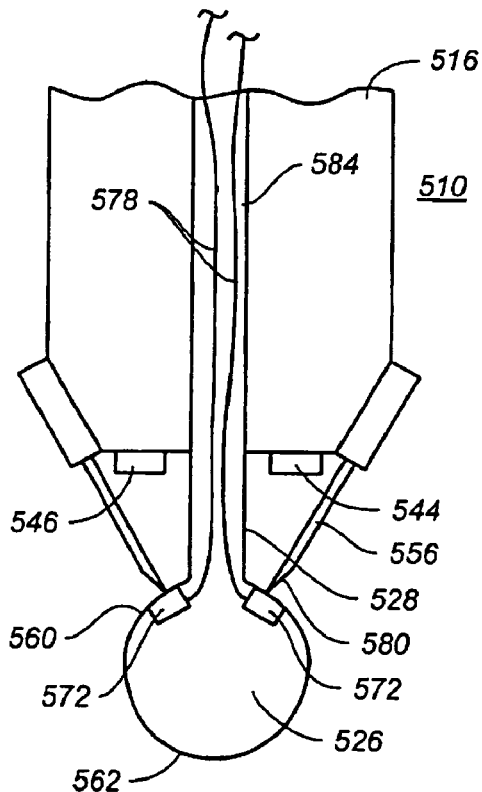
FIG._30

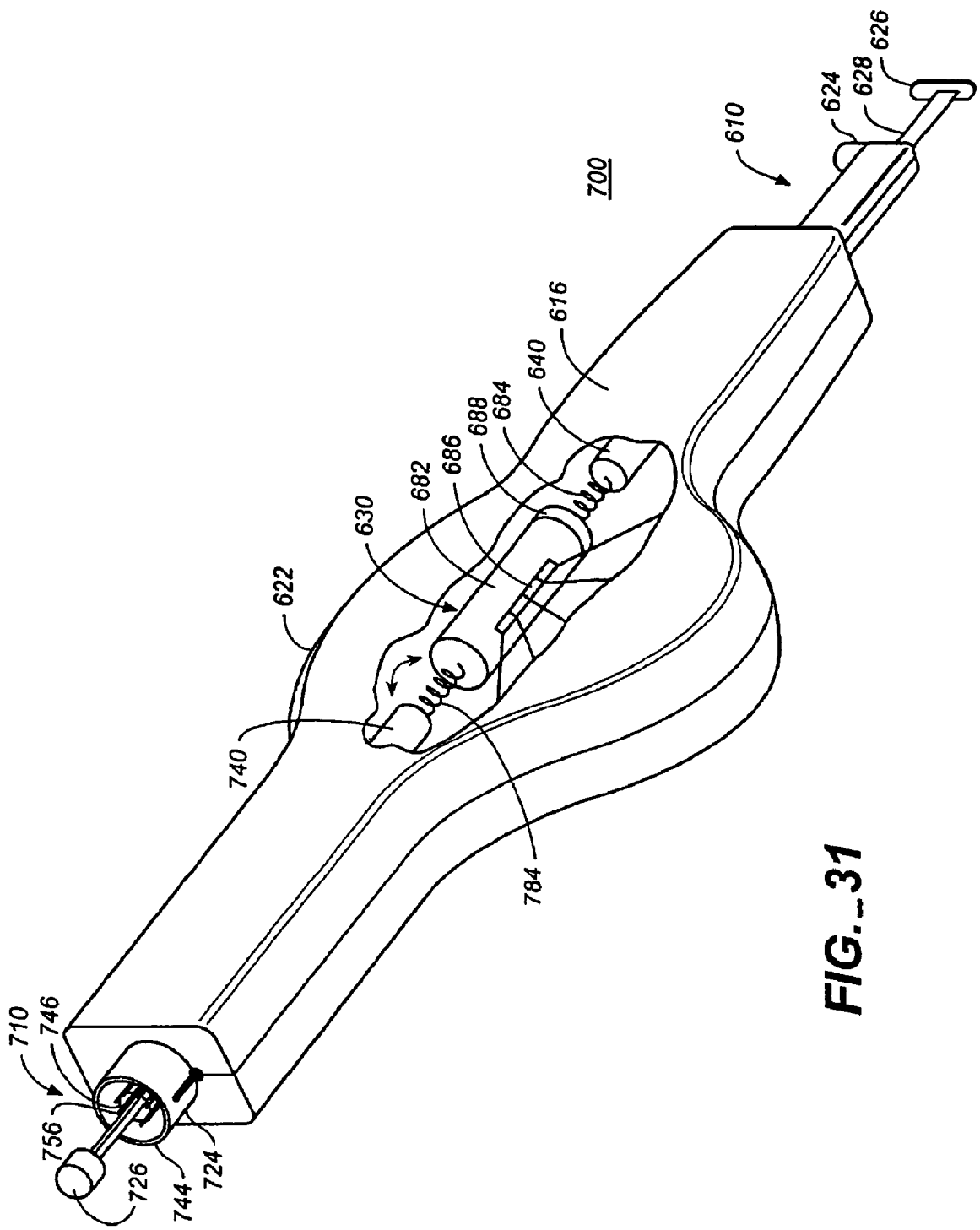
FIG._31

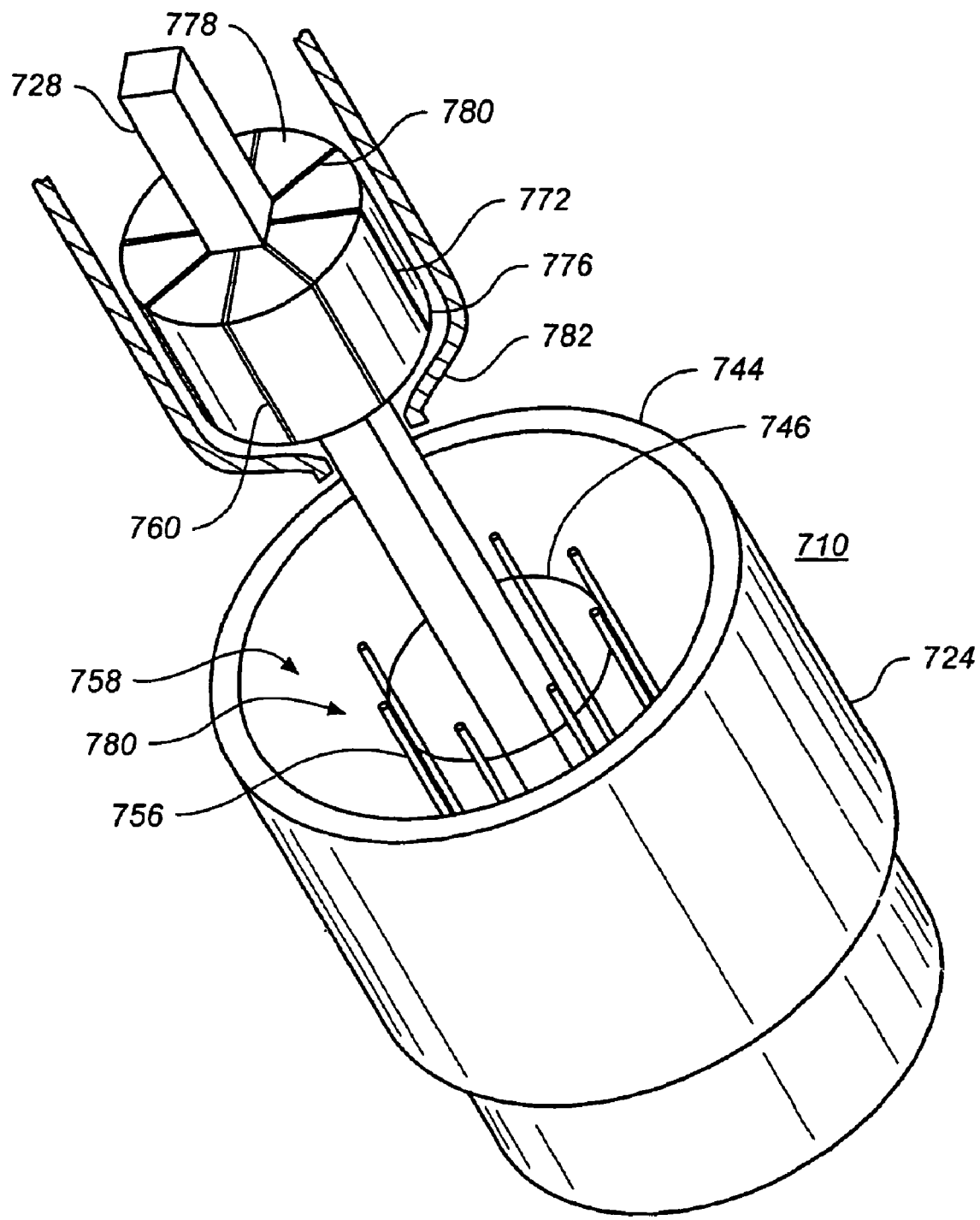
FIG._32

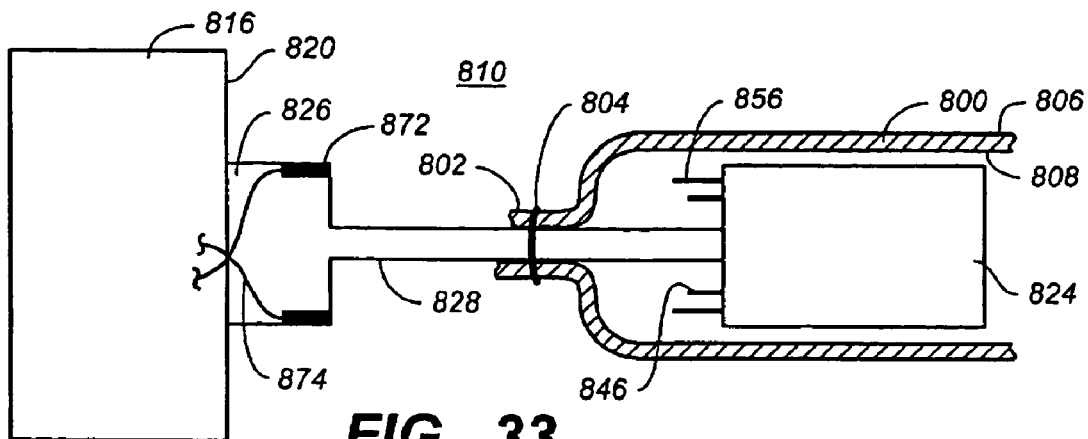
FIG._33
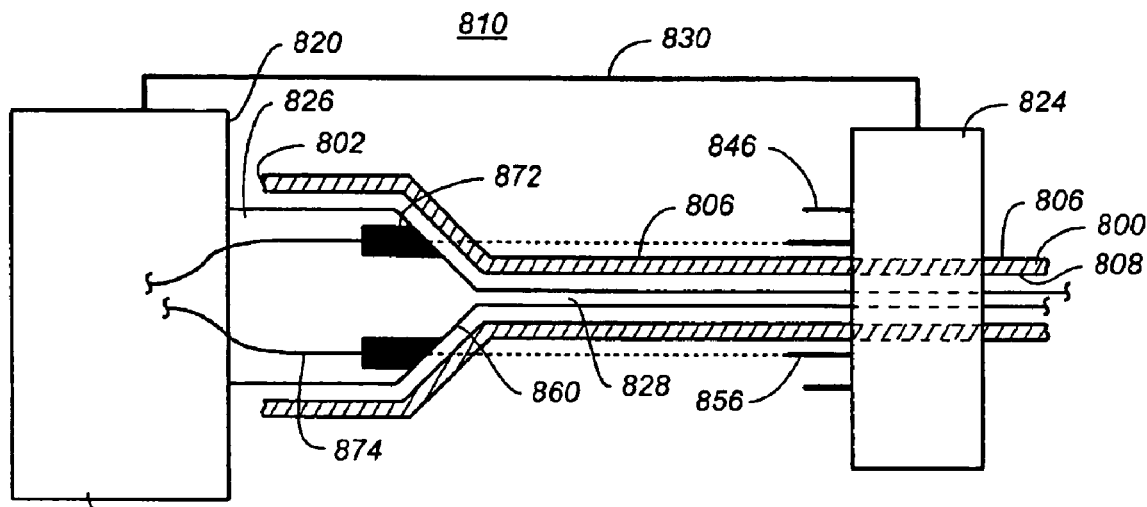
FIG._34
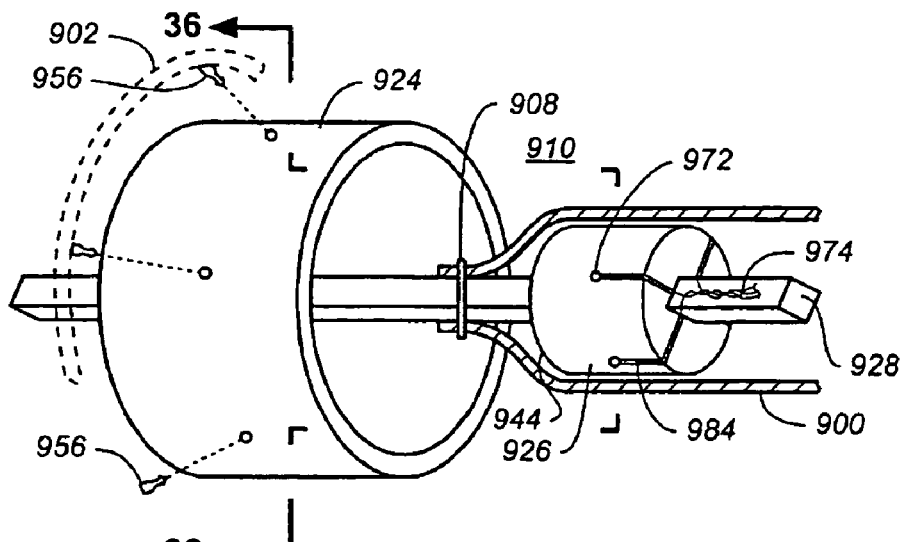
FIG._35

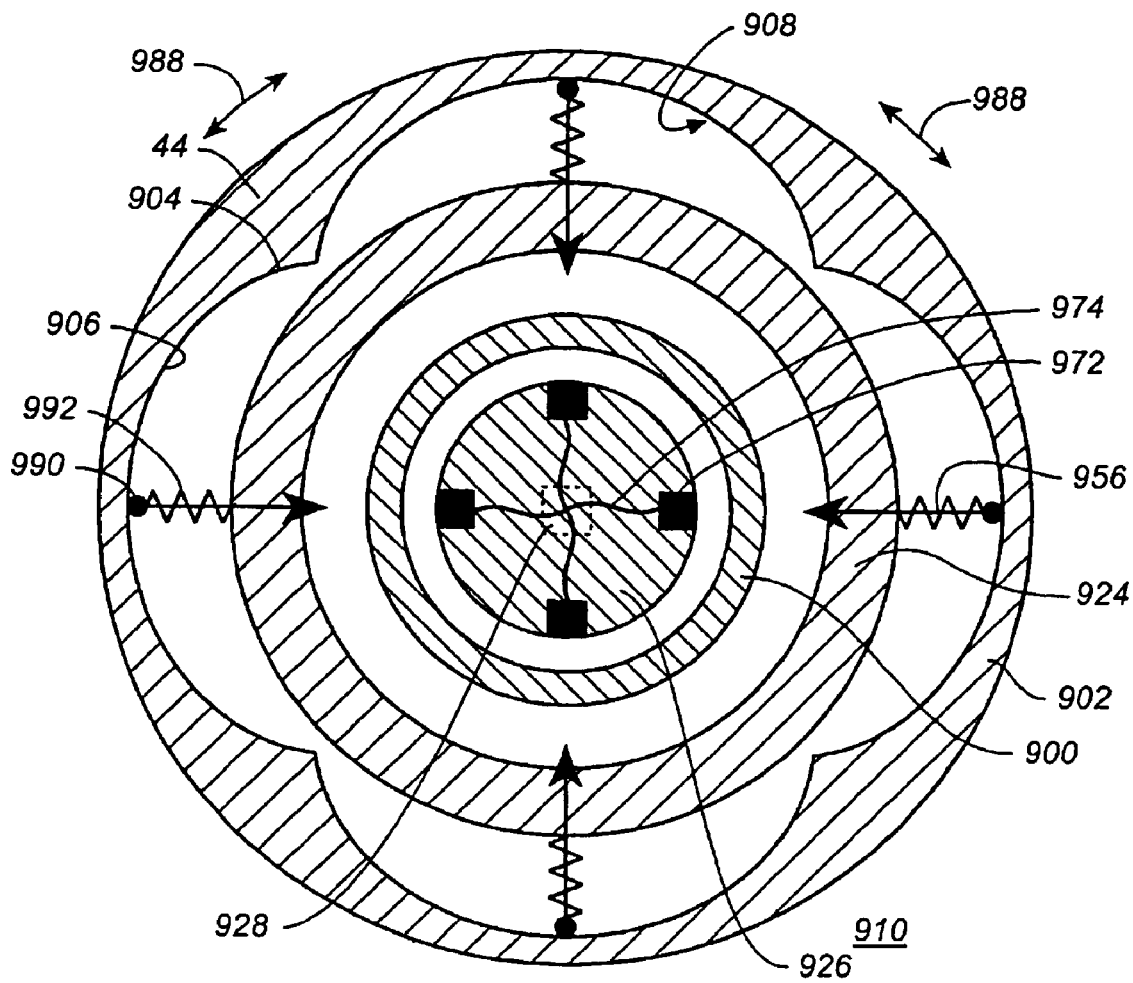
FIG._36
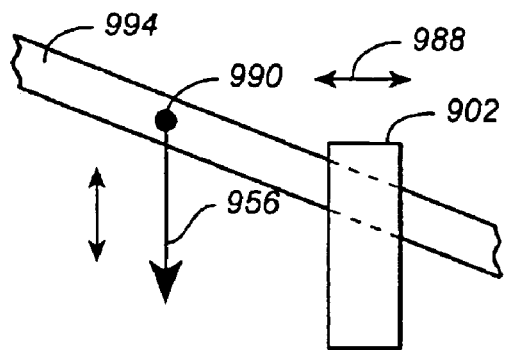
FIG._37

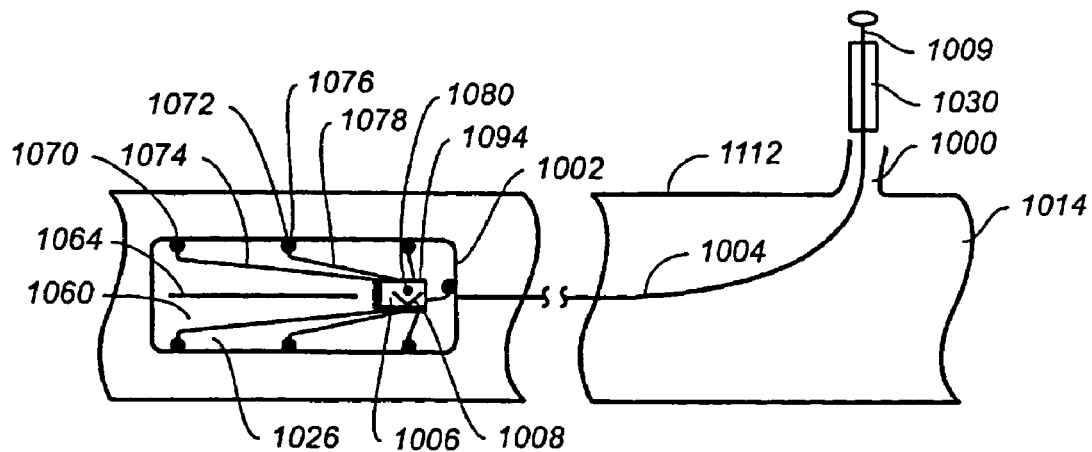
FIG._38
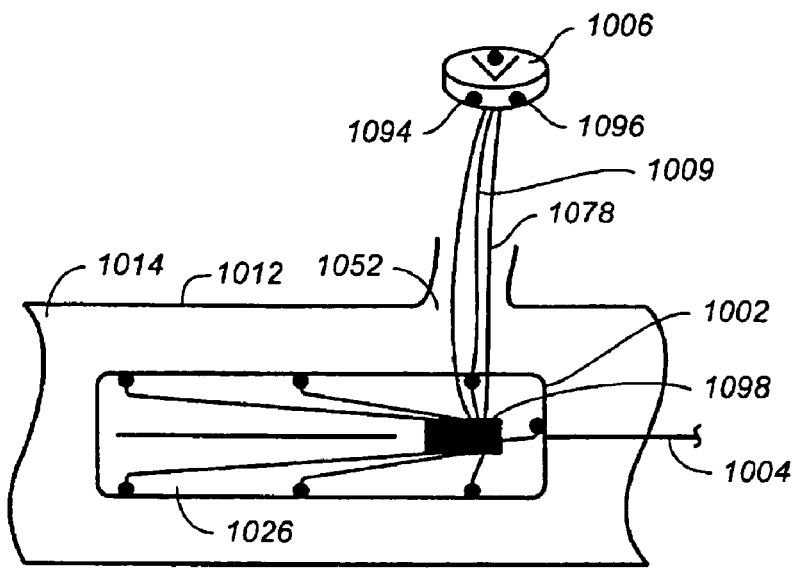
FIG._39
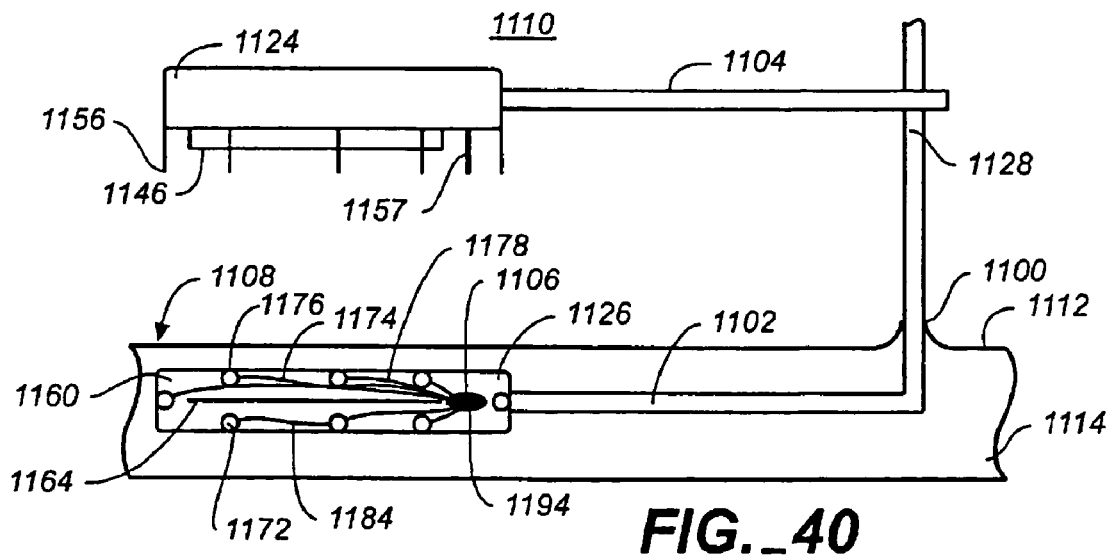
FIG._40

DEVICE AND METHOD FOR SUTURING TISSUE

RELATED APPLICATIONS

This application is a continuation of U.S. patent application Ser. No. 10/033,689, filed Dec. 28, 2001, now abandoned, which is a continuation of U.S. patent application Ser. No. 08/883,246, filed Jun. 26,1997, now U.S. Pat. No. 6,355,050, which is a continuation-in-part of U.S. patent application Ser. No. 08/824,031, filed Mar. 26, 1997, now U.S. Pat. No. 6,036,699, which is a continuation-in-part of U.S. patent application Ser. No. 08/259,410, filed Jun. 14, 1994, now U.S. Pat. No. 5,779,719, which is a divisional and a continuation-in-part of U.S. application Ser. No. 07/989,611, filed Dec. 10, 1992, now U.S. Pat. No. 5,417,699. These prior applications are hereby incorporated fully herein by reference.

FIELD OF THE INVENTION

The present invention relates generally to devices and methods for the suturing of tissue in various applications such as closure of arterial and venous puncture sites, suturing a graft anastomosis to an aperture in a vessel wall or other types of tissue, and the like. More particularly, the inventive devices and methods provide for suturing the tissue of a vessel even though the vessel may be under physiological flow and while preferably maintaining hemostasis.

BACKGROUND OF THE INVENTION

A number of diagnostic and interventional vascular procedures are now performed transluminally, where a catheter is introduced to the vascular system at a convenient access location and guided through the vascular system to a target location using established techniques. Such procedures require vascular access which is usually established using the well known Seldinger technique, as described, for example, in William Grossman's "Cardiac Catheterization and Angiography," 3rd Ed., Lea and Febiger, Philadelphia, 1986, incorporated herein by reference.

When vascular access is no longer required, the introducer sheath must be removed and bleeding at the puncture site stopped. One common approach to attempt providing hemostasis (the cessation of bleeding) is to apply external force near and upstream from the puncture site, typically by manual or "digital" compression. This approach suffers from a number of disadvantages. It is time-consuming, frequently requiring one-half hour or more of compression before hemostasis is assured. This procedure is uncomfortable for the patient and frequently requires administering analgesics to be tolerable. Moreover, the application of excessive pressure can at times totally occlude the underlying blood vessel, resulting in ischemia and/or thrombosis. Following manual compression the patient is required to remain recumbent for at least six and at times as long as eighteen hours under close observation to assure continued hemostasis. During this time renewed bleeding may occur resulting in bleeding through the tract, hematoma and/or pseudoaneurysm formation as well as arteriovenous fistula formation. These complications may require blood transfusion and/or surgical intervention. The incidence of these complications increases when the sheath size is increased and when the patient is anti-coagulated. It is clear that the standard technique for arterial closure can be risky, and is expensive and onerous to the patient. While the risk of such conditions can be reduced by using highly trained individuals, such use is both expensive and inefficient.

To overcome the problems associated with manual compression, the use of bioabsorbable fasteners to stop bleeding has been proposed by several groups. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel, and locating the fastener too far from that surface can result in failure to provide hemostasis and subsequent hematoma and/or pseudo aneurism formation. Conversely, if the fastener intrudes into the arterial lumen, intravascular clots and/or collagen pieces with thrombus attached can form and embolize downstream causing vascular occlusion. Also, thrombus formation on the surface of a fastener protruding into the lumen can cause a stenosis which can obstruct normal blood flow. Other possible complications include infection as well as adverse reactions to the collagen implant.

Catheters are also used to treat heart disease which is a major medical ailment wherein arteries become narrowed or blocked with a build-up of atherosclerotic plaque or clot which reduces flow to tissues downstream or "distal" to the blockage. When this flow reduction becomes significant, a patient's quality of life may be significantly reduced. In fact, heart disease patients often die when critical arteries, such as the coronary arteries, become significantly blocked.

However, technology has been developed to open some blocked arteries in the treatment of heart disease. For example, balloon angioplasty has become a well accepted treatment wherein a balloon is inflated within the narrowed vessel to stretch or otherwise deform the blockage into a larger lumen. Attentively, the blockage can even be removed, such as in a procedure known as atherectomy. In general, these treatments use percutaneous catheters which are inserted into the patients' vessels at a peripheral artery or vein puncture site and guided to the internal blockage site via x-ray visualization. The blockage is then treated remotely by use of hydraulic pressure in the case of balloon angioplasty, or by other actuating means to cause remote cutting or ablation of the blockage in the case of atherectomy.

Coronary Artery Bypass Graft Surgery ("CABG")

In the alternative to using catheters to treat heart disease, or when such catheterizations are contraindicated, some blocked vessels can be treated with coronary artery bypass graft surgery ("CABG"). In conventional CABG techniques, a tubular graft is affixed to a port or aperture in an artery wall distally of the blockage. When the opposite end of the tube is in fluid communication with a pressurized arterial blood supply, such as the aorta, the tubular graft provides a conduit for flow into the vessel lumen distally of the blockage.

Conventional CABG surgery is generally initiated by directly exposing the heart to the surgeon. This is accomplished by opening the patient's chest using known sternotomy and retraction techniques that cut the sternum and spread the rib cage open. Then, one or both lungs are usually deflated and the patient is connected to a respiratory assist machine.

Once the heart is exposed, the patient is connected to a coronary bypass machine so that the blood supply circumvents the heart. In this way, the heart is depressurized so that apertures can be cut into the walls of the vessels for surgical graft attachment. The right atrium (or vena cava) and the aorta each is intubated with cannulas which are connected to an artificial pump and oxygenator. Once these major vessels are cannulated, cardioplegia is delivered to slow or stop the beating motion of the heart. The aorta is then clamped proximally of the aortic bypass cannula, thereby isolating the proximal aortic root from the blood that is being circulated by the bypass machine.

After the heart is isolated from blood pressure, conventional bypass grafting is performed. The required grafts are implanted to feed the coronary arteries distal to the blockage, the clamp is removed from the aorta, the lungs are restored, and the patient is then taken off of the bypass pump.

In one type of CABG method, the bypass grafting is achieved between the aorta and one of the three major coronary arteries or their sub-branches, the left anterior descending artery (LAD), the circumflex artery (CIRC), or the right coronary artery (RCA). In such a case, a saphenous vein is usually taken from the patient's leg and is transplanted as a "homograft" to connect these vessels in the same patient's chest. Artificial grafts have also been disclosed as providing potential utility for this purpose and are herein collectively included in the general discussion of "saphenous veins" as used in CABG procedures.

An alternative CABG method uses the internal mammary artery (IMA) alone or in conjunction with the saphenous vein graft. The IMA is severed at a chosen location and is then connected to an aperture, in a coronary artery.

In either case of using saphenous vein homografts or artificial grafts in CABG surgery, the proximal end of the graft is generally sutured or otherwise is affixed circumferentially to the tissue surrounding an aperture that is punched into the wall of the aorta. In this arrangement, the lumen of the graft communicates with the vessel through the aperture, wherein ideally the aperture approximates the inner diameter of the graft lumen. The opposite, distal end of the graft is sutured to an aperture formed in the wall of the coronary vessel distal to the blockage.

The fluid connections between a graft and a vessel are herein referred to as "anastomoses." In the instance of CABG, "proximal anastomoses" and "distal anastomoses" are terms used when referring to grafting to the aorta and the coronary artery, respectively. In most CABG procedures using saphenous vein grafts, the distal anastomosis is performed first, followed by the proximal anastomosis.

For the CABG method using the IMA, only one distal anastomosis is formed distal to the arterial blockage. A proximal anastomosis to the aorta is not required as it is in a saphenous vein graft procedure because the IMA's natural arterial blood flow feeds the heart.

In conventional CABG surgery methods such as those just summarized, the timing and technique of the anastomosis procedures are critical factors to procedural success. In fact, it is believed that three critical determinants which affect outcomes of CABG surgery are: (1) time the patient spends on bypass, (2) time the patient spends with a clamped aorta, and (3) the quality of the anastomoses. It is generally believed that a CABG patient's operative and peri-operative morbidity are directly related to how long the patient must be on heart bypass. In fact, it is generally understood that the risk of patient morbidity is believed to rise significantly after a threshold time of one hour on bypass. Perhaps the most prevalent complication arising from prolonged cardiac bypass is the high risk of distal thrombus created by the artificial plumbing. For example, such thrombi can embolize into the neurovasculature and potentially can cause a stroke. In analyzing the timing of individual CABG steps against the backdrop of a patient's critical time on bypass, the time spent anastomosing the grafts to vessels emerges as a controlling factor. The average time for suturing one anastomosis is approximately 7-10 minutes. Furthermore, it is believed that an average CABG procedure involves approximately five anastomoses: two saphenous vein grafts, each with a proximal and a distal anastomosis, and one internal mammary artery having only one distal anastomosis. Therefore, the average time for graft suturing ranges from 35 minutes to 50 minutes—in any case a significant portion of the 60 minute critical threshold to patient morbidity. Closely related to the time spent on bypass is a second CABG success factor related to the extent and time of aortic cross-clamping. It is believed that the inherent crushing force from a cross-clamp across the bridge of the muscular aortic arch may be associated with a high degree of tissue trauma and structural damage. Additionally, hemostasis formed at or adjacent to the cross clamp, perhaps in conjunction with the tissue trauma of clamping, may also be a source of unwanted thrombogenesis.

In addition to the timing of anastomosing grafts and extent and duration of aortic cross-clamping, the quality of interface between the graft and vessel is also believed to be an indicator of procedural success. The accuracy, trauma, and repeatability of suturing, as well as the three-dimensional interface formed between the conduits at the anastomosis site, are significant variables in conventional manual surgical techniques. These variables are believed to significantly affect the short or long-term success of conventional CABG anastomosis procedures.

Limitations of Conventional CABG Devices & Methods

Both of the critical CABG success indicators summarized above—time on cardiac bypass and quality of anastomosis suturing—are directly affected by inherent limitations in the devices used in conventional CABG procedures. It is believed that improvements to these devices and related methods of use may provide for more rapid and reliable vessel-graft anastomosing. For example, conventional "surgical punches" are devices that cut or "punch" a plug in vessel wall tissue to form an aperture in the wall. In a CABG procedure, the tissue surrounding a punched-out aperture provides the substrate upon which a graft may be sutured to form an anastomosis. One procedural limitation in using conventional surgical punches is that hemostasis can not be maintained at a vessel wall after a plug of tissue is punched out and removed. Therefore, an aperture in an aortic wall during a saphenous vein graft procedure can only be made when that portion of the aorta is cross-clamped, bypassed, and depressurized. Otherwise, the high blood pressure and flow in the aorta would cause significant bleeding during the period from punching the aperture to forming the anastomosis. Because of this limitation in conventional surgical punches, the threshold 60 minute coronary bypass clock begins running before punching the aorta.

The prior art fails to disclose or fulfill the need which exists in the field of medical devices and methods for: suturing tissue by proximally drawing sutures through a tissue layer in the proximity of an aperture; suturing tissue by reversibly advancing needles from one side of a tissue layer to retrieve one or more sutures on the opposite side of the tissue layer; a medical device assembly and method that automatically and repeatably places suture thread through vessel wall tissue surrounding an aperture in the vessel wall in a suture pattern that is useful for anastomosing a tubular graft to the aperture; and a medical device assembly that deploys a suture with one end extending through the tissue that surrounds a aperture in a vessel wall and the opposite suture end extending radially through a tubular graft wall adjacent an open end of the graft, such that a vessel anastomosis may be rapidly and repeatably performed in a CABG procedure even while the vessel is under physiological flow.

SUMMARY OF THE INVENTION

The present invention provides a device for suturing a tissue layer having two sides which includes a suture and means for releasably retaining at least a portion of the suture in a stationary position on one side of the tissue layer. The device also includes means for retrieving the portion of the suture through the tissue layer from the opposite side whereby the suture is drawn from one side to the opposite side.

A device is also provided for suturing at least one tissue layer wherein each tissue layer has two sides. The device includes a fastener having at least a first and second portion. The first and second portions have means for securing the first and second portions together. The first and second portions have a base at one end to prevent the respective portion from passing completely through the tissue layer. The device includes means for releasably retaining the first portion in a stationary position on one side of the tissue layer and means for driving the second portion through the tissue layer from the opposite side and securely engaging the securing means of the first and second portions whereby the base of the first portion abuts one side of the tissue layer and the base of the second portion abuts the opposite side of the tissue layer.

The present invention provides a device for suturing tissue in the proximity of an aperture in a tissue layer which include a shaft having a proximal and distal end and a foot attached to the distal end of the shaft. The foot is adapted for advancing through the aperture. At least one needle is carried above the distal end of the shaft. At least a portion of a suture is releasably retained on the foot in the proximity of the aperture. The device also includes means for reversibly advancing the needle through the tissue to retrieve and draw at least a portion of the suture through the tissue. The advancing means is integrally formed with the shaft.

A device for suturing the wall of a tubular graft having two sides is also provided by the present invention. The device includes a suture, means for releasably retaining at least a portion of the suture on one side of the wall, and means for retrieving the portion of the length of suture through the wall of the graft to the opposite side of the wall.

A graft anastomosis assembly is also provided for suturing a tubular graft about an aperture in a tissue wall. The assembly includes a suture, a tissue suturing and graft suturing devices. The tissue suturing device includes means for releasably retaining at least a portion of the suture in a stationary position on one side of the tissue layer and means for retrieving the portion of the suture through the tissue layer from the opposite side whereby the suture is drawn from one side to the opposite side. The graft suturing device includes means for releasably retaining at least a portion of the suture on one side of the graft and means for retrieving the portion of the length of suture through the wall of the graft to the opposite side of the graft.

A graft assembly for anastomosing a tubular graft and vessel is also disclosed herein. The graft having a graft wall that defines a graft lumen with an open end. The graft wall has a plurality of ports spaced in a predetermined pattern near the open end. The assembly includes a plurality of sutures in the predetermined pattern. Each suture has a first suture portion extending through one of the plurality of ports in the graft wall. Each suture has a second suture portion extending along at least a portion of the graft lumen.

A method for suturing a tissue layer having two sides is also provided by the present invention. The steps of the method include: releasably retaining at least a portion of a suture in a stationary position on one side of the tissue layer; and retrieving at least a portion of the suture through the tissue layer to the opposite side.

Another method of the present invention sutures tissue in the proximity of an aperture in a tissue wall. The steps of the method include: forming a port from the proximal side of the tissue wall; passing at least a portion of a suture from the distal side of the tissue wall proximally through the port in the tissue wall in the proximity of the aperture; and forming a loop with the remaining portion of the suture to secure the suture.

A further method for suturing an aperture in a vessel wall is provided herein. The steps of the method include: reversibly advancing a plurality of needles through the vessel wall to form ports in the proximity of the aperture; passing at least a portion of a suture proximally through the ports in the vessel wall disposed on opposite sides of the aperture from the interior of the vessel with the remaining portion of the suture passing out of the vessel; and securing the ends of the suture to close the aperture.

Another method of the present invention sutures the wall of a tubular graft to define a graft lumen and an open graft end. The steps of the method include: releasably retaining at least a portion of a suture within the graft lumen and adjacent the graft open end; puncturing the tubular graft wall with the plurality of needles to form a plurality of ports in a circumferential pattern; and drawing the portion of suture outwardly from the graft lumen and through each of the plurality of ports and external of the graft wall.

BRIEF DESCRIPTION OF THE DRAWINGS

In the drawings, which comprise a portion of this disclosure but are not to scale:

FIG. 9 is a perspective view of a tissue suturing device of the present invention inserted through a tissue layer;

FIG. 10 is an isolated perspective view of the needle carrier and foot of the tissue suturing device in FIG. 9;

FIG. 11 is a top view of the foot of the tissue suturing device in FIG. 9;

FIG. 12 is a side view of the foot and shaft of the tissue suturing device in FIG. 9 inserted through a tissue layer;

FIG. 13 is an isolated perspective view of an alternate embodiment of the shaft and foot of the tissue suturing device;

FIG. 14A is a cross-sectional view of the foot along the lines 14A-D in FIG. 13 illustrating an example of one cross-sectional shape for the foot;

FIG. 14B is a cross-sectional view of the foot along the lines 14A-D in FIG. 13 illustrating another example of one cross-sectional shape for the foot;

FIG. 14C is a cross-sectional view of the foot along the lines 14A-D in FIG. 13 illustrating another example of one cross-sectional shape for the foot;

FIG. 14D is a cross-sectional view of the foot along the lines 14A-D in FIG. 13 illustrating another example of one cross-sectional shape for the foot;

FIG. 15 is a side view isolating the engagement of a needle and suture of the tissue suturing device illustrated in FIG. 9;

FIG. 16 is a cross-sectional view of the needle and suture in FIG. 15 along the lines 16-16 with the needle and suture in an engaged position;

FIG. 17 is a top view of the needle and suture in FIG. 15 along the lines 17-17 with the needle and suture in an engaged position;

FIG. 18A is a side view of the suture end illustrating an example of a ball shape for the suture end;

FIG. 18B is a side view of the suture end illustrating an example of a solid cuff shape for the suture end;

FIG. 18C is a side view of the suture end illustrating an example of a ring shape for the suture end;

FIG. 18D is a side view of the suture end illustrating an example of a serrated cuff shape having slits for the suture end;

FIG. 18E is a side view of the suture end illustrating an example of a hook shape for the suture end;

FIG. 19A is a side view of a serrated needle tip illustrating an example of a retrieving device of the present invention;

FIG. 19B is a side view of a needle tip and tubing assembly illustrating an example of another retrieving device of the present invention;

FIG. 19C is a side view of a needle tip with an indentation illustrating an example of another retrieving device of the present invention;

FIG. 19D is a side view of a hook-shaped needle tip illustrating an example of another retrieving device of the present invention;

FIG. 19E is a side view of a needle tip and tubing assembly illustrating an example of another retrieving device of the present invention;

FIG. 20 is a cross-sectional view of two tissue layers being joined by the present invention using a multi-piece fastener in a tissue suturing device;

FIG. 21 is a cross-sectional view of a tissue layer and suture being joined by the present invention using a multi-piece fastener in a tissue suturing device;

FIG. 22 is a cross-sectional view of a suture cuff attached to two lengths of a suture for use with the present invention;

FIG. 23 is a top view of an isolated section of tissue layer having a suture pattern therein formed by a continuous suture used with the present invention;

FIG. 24 is a top view of an isolated section of tissue layer having a purse-string suture pattern therein formed by a single suture used with the present invention;

FIG. 25 is a perspective view of another embodiment of a tissue suturing device of the present invention;

FIG. 26 is an isolated top view of the foot of the tissue suturing device of FIG. 25;

FIG. 27 is a cross-sectional view of an alternate button embodiment for retrieving a suture loop in the foot of the present invention;

FIG. 28 is a top view of a tear shaped button embodiment for retrieving a suture loop in the foot of the present invention;

FIG. 29 is a cross-sectional view of the button embodiment in FIG. 27 for retrieving a suture loop in the foot of the present invention;

FIG. 30 is a diagrammatic side view of another embodiment of a tissue suturing device of the present invention utilizing a needle carrier and needle retrieval arrangement positioned at an obtuse angle to the longitudinal axis of the device;

FIG. 31 is a perspective view of an anastomoses assembly of the present invention;

FIG. 32 is an isolated perspective view of the graft suturing device from the assembly in FIG. 31;

FIG. 33 is another embodiment of a graft suturing device of the present invention which retrieves sutures inwardly through a graft wall;

FIG. 34 is another embodiment of a graft suturing device of the present invention which positions the graft through the needle carrier;

FIG. 35 is a perspective view of another embodiment of the graft suturing device of the present invention which retrieves the sutures in an axial direction;

FIG. 36 is a cross sectional view of a needle driving device for retrieving the sutures illustrated in FIG. 35;

FIG. 37 is a side view of an alternate arrangement for driving the needles as illustrated in FIG. 36;

FIG. 38 is a cross-sectional view of a vessel illustrating the insertion of a foot of the inventive tissue suturing device from a remote access site;

FIG. 39 is a cross-sectional view of a vessel illustrating the insertion of a foot of the inventive tissue suturing device from a remote access site; and FIG. 40 is a cross-sectional view of a vessel illustrating the insertion of another embodiment of a foot of the inventive tissue suturing device from a remote access site.

DETAILED DESCRIPTION OF THE INVENTION

Figure 1:
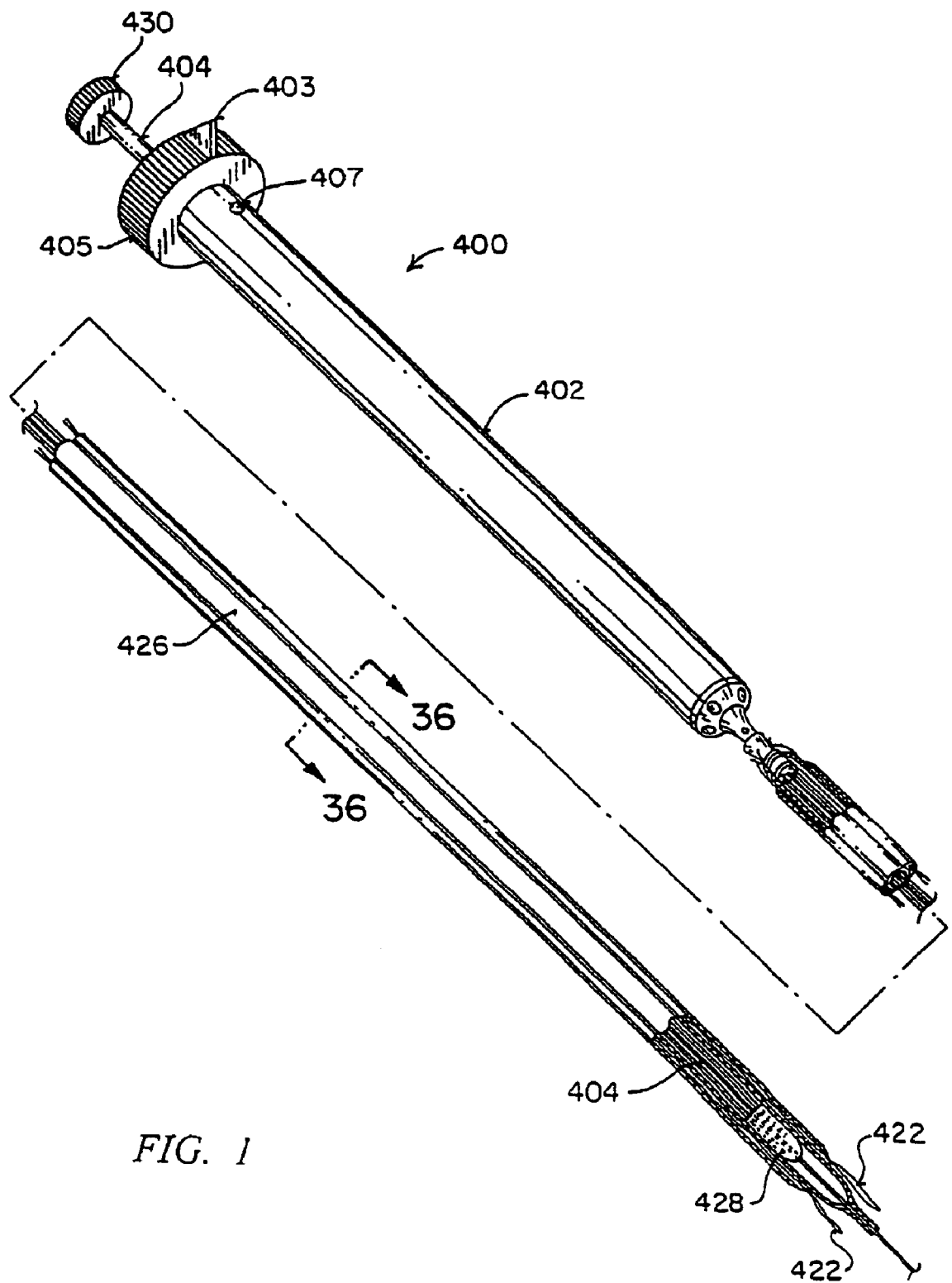
FIG. 1 is a perspective view of an embodiment of a suturing device constructed in accordance with the principles of the present invention.

As used herein, the term "distal" is generally defined as in the direction of the patient, or away from a user of a device, or in a downstream direction relative to a forward flow of blood. In the context of a medical device intervention with or through a vessel wall, "distal" herein refers to the interior or the lumen side of the vessel wall.

Conversely, "proximal" generally means away from the patient, or toward the user, or in an upstream direction relative to a forward flow of blood. In the context of a medical device intervention with or through a vessel wall, "proximal" herein refers to the exterior or outer side of the vessel wall.

Additionally, "oblong" is herein intended to mean oval, elliptical, or otherwise having a generally rounded shape that is not perfectly circular. In particular, the term describes the shape of a tubular graft end cut at an acute angle relative to the plane perpendicular to the tissue walls defining the graft.

The term "hemostasis" is herein used to mean the arrest of bleeding or substantially blocking flow of blood outwardly from a vessel lumen while the vessel lumen is pressurized or sustaining physiological blood flow. This amount of blockage or occlusion to flow is further defined such that the blood loss which is experienced is less than an amount which would affect procedural methods or outcomes according to a physician user of a device of ordinary skill in the art. In other words, "hemostasis" is not intended to mean only "total hemostasis" such that there is a total lack of blood loss. Rather, the term is used to also mean "procedural hemostasis" as a relative term in its use among physicians of ordinary skill.

Similarly, "occlusion," "occlude," "blockage," "block . . . plugging", "block," or variations thereof are all terms which are herein intended to have a procedurally relevant definition in the context of their use. For instance, an aperture is "occluded" although there is some measurable flow therethrough, but that flow is so low such that the intended procedural benefit of occlusion is at least partially achieved. Certainly, such terms also properly include within their scope a "total effect" definition, as well.

The term "perfusion" is herein used to mean the flow of blood or other unit of perfusate (the fluid used for perfusion) per unit volume of tissue. Physiological perfusion refers to the amount of blood flow present when the body is functioning normally. For example, physiological perfusion usually prevents clinically significant ST elevations which is one of the most sensitive indicators of inadequate perfusion. Adequate perfusion refers to the amount of blood flow that avoids the clinical requirement of transfusing the patient or that is needed to prevent tissue necrosis distal to the aperture in the blood vessel.

The term "suturing" is herein intended to include the process of joining two surfaces or edges together with a fasten r so as to close an aperture, opening, or wound or join tissues. The fastener is usually a suture such as a thread of material (either polymeric or natural), gut, wire or the like. The term fastener as used herein also includes clamps, studs, hasps, catches, hooks, rivets, staples, snaps, stitches, VELCROC™, buttons, and other coupling members.

Figure 2A:
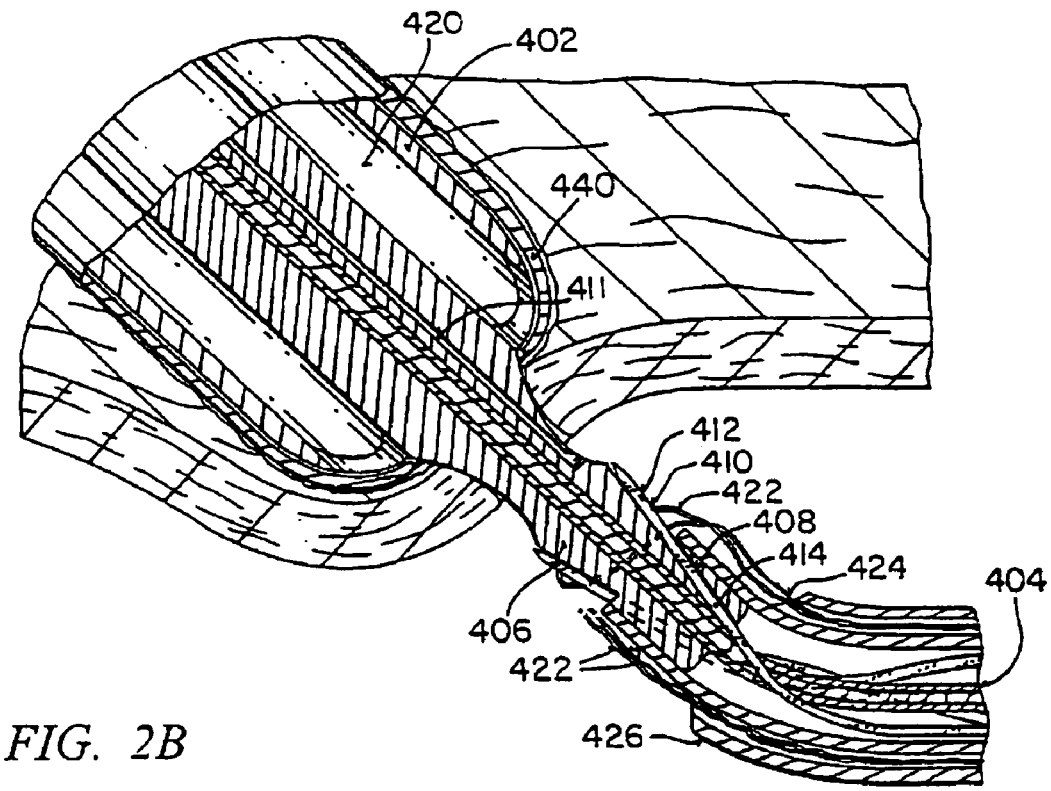
FIG. 2A is a detail view of the distal end of the guide body of the suturing device of FIG. 1, shown with the needles retracted fully within the guide body.
Figure 2B:
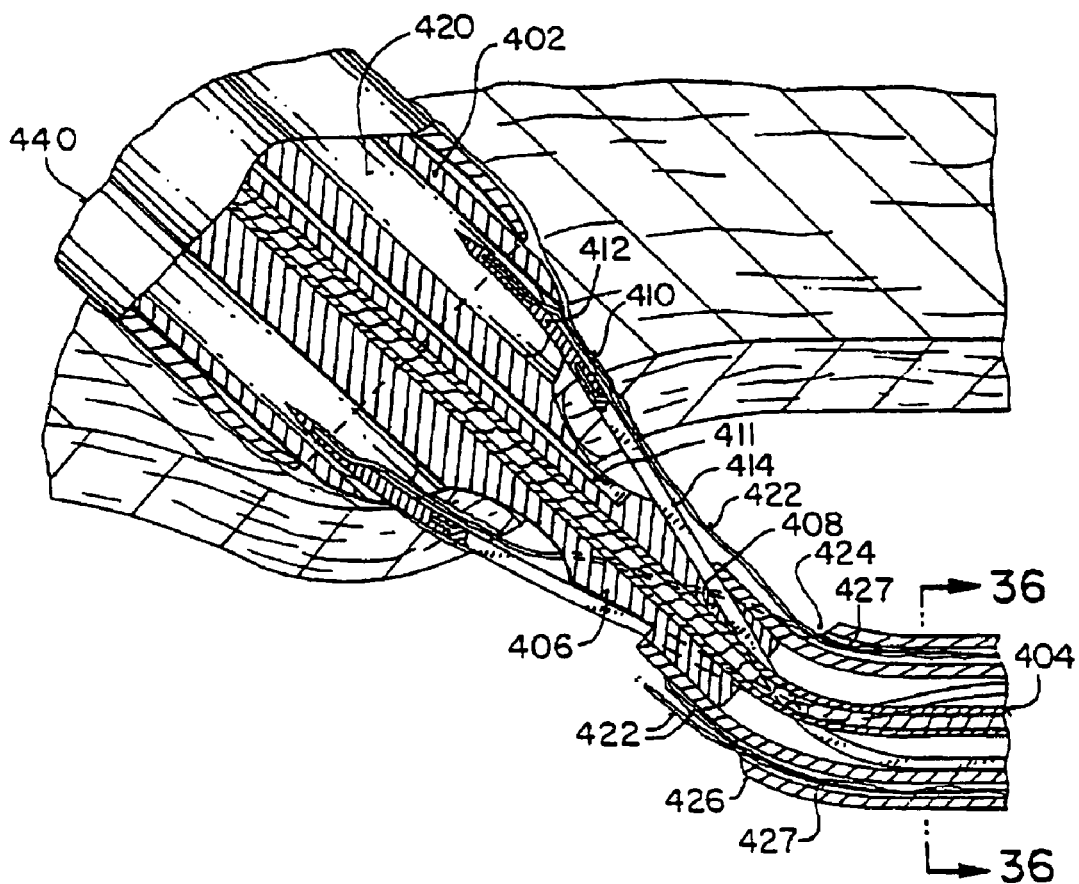
FIG. 2B is a view similar to FIG. 2A, except that the needles have been partially drawn back into the guide body.
Figure 3:
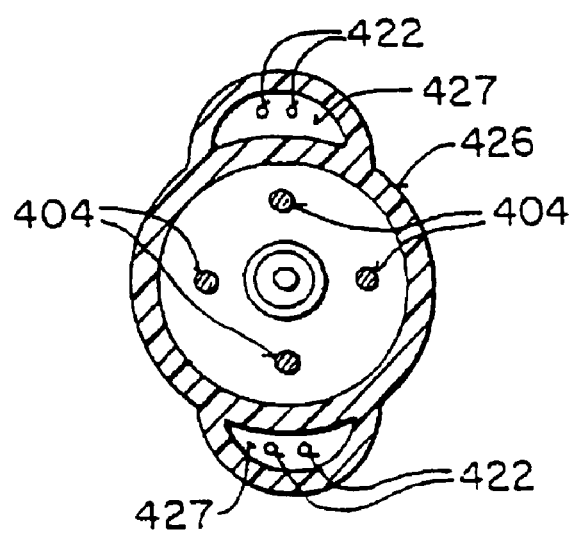
FIG. 3 is a cross-sectional view of the device of FIGS. 2A and 2B, taken along line 3-3 of FIG. 2B.

Referring to FIGS. 1-3, a suture applying device 400 which is suitable for suturing and sealing of percutaneous vascular puncture site, particularly those made to the femoral artery in a patient's groin, will be described. It will be appreciated, however, that the device of the present invention can be readily adapted for use with punctures made to other hollow body organs and lumens, although it may be necessary to modify the dimensions and other particular aspects of the device to accommodate the different usage environment.

The device 400 comprises a guide body 402 and a needle shaft 404. The guide body 402 includes a guide tip 406 at its distal end, which guide tip includes a plurality of guide channels 408 which receive the proximal ends of needles 410. An aligning arrow 403 is mounted on handle 405 located at the proximal end of the guide body 402. A marker lumen bubble 407 is located below the aligning arrow and serves to indicate when the distal end of the guide body has entered a blood vessel, as described in the embodiment below. An indicator lumen 411 which permits the flow of blood to the marker lumen bubble 407 is illustrated in FIGS. 2A and 2B.

The needles 410 as illustrated comprise a sharpened tip section 412 and an elongate shank portion 414, but may also be manufactured as an integral piece. The shank portion 414 will be sufficiently long so that the needles may be pushed from their butt end by a support holster 428 fixedly attached to the needle shaft 404 in order to advance the needles through the tissue to be sutured and fully through the guide body 402 inserted together with support sheath 440 in the associated tract so that no capture mechanism will be required.

The guide body 402 further includes a plurality of needle lumens 420 which are axially aligned and spaced about the periphery of the guide body. As best seen in FIG. 2B, the needles 410 will enter the distal ends of the lumens 420 as the needles are advanced proximally relative to the guide body.

A flexible needle sheath 426 will be attached to the guide tip 406 of guide body 402. The central lumen of the needle sheath 426 receives a support holster 428 attached to the distal end of the needle shaft 404, as well as the needles 410. As with previous embodiments, the butts of the needles 410 are removably received within the support holster 428. The sheath 426 will be sufficiently long to permit the needles to extend at least 5 cm beyond the distal end of guide body 402.

Prior to use, the suture applying device 400 will be in the configuration illustrated in FIGS. 1 and 2A. That is, the needle shaft 404 will be distally positioned within the guide body 402 and needle sheath 426. In particular, the tips of needles 412 will lie just at the guide tip 406 so that they may be easily advanced through the arterial tissue surrounding the arteriotomy. That is, the tips of the needles will be generally retracted within the guide tip 406. A length of suture 422 is attached to the proximal tips 412 of opposed pairs of needles 410, with the connecting suture being stored in side lumens 427 extending axially along the exterior of the needle sheath 426. As best observed in FIGS. 2A and 2B, the suture 422 extending between one pair of opposed needles is received in a first of the side lumens 427, while the suture extending between the other pair of opposed needles is received in the second of the side lumens. While it would be possible to store the suture 422 in the lumens 420 of the guide body 402 (and thus eliminate the need for side lumens 427), such storage is less preferred since it increases the risk that the suture will become entangled with the needles 410 as they are withdrawn proximally. The use of side lumens 427 greatly simplifies feeding of the suture as the needles 410 are withdrawn.

After the guide tip 406 has been passed through the puncture site to be sutured, the needles may then be drawn proximally forward through the tissue to be sutured by drawing proximally on handle 430 at the proximal end of needle shaft 404. The method of the present invention will now be described in more detail with reference to FIGS. 4-7.

Figure 4:
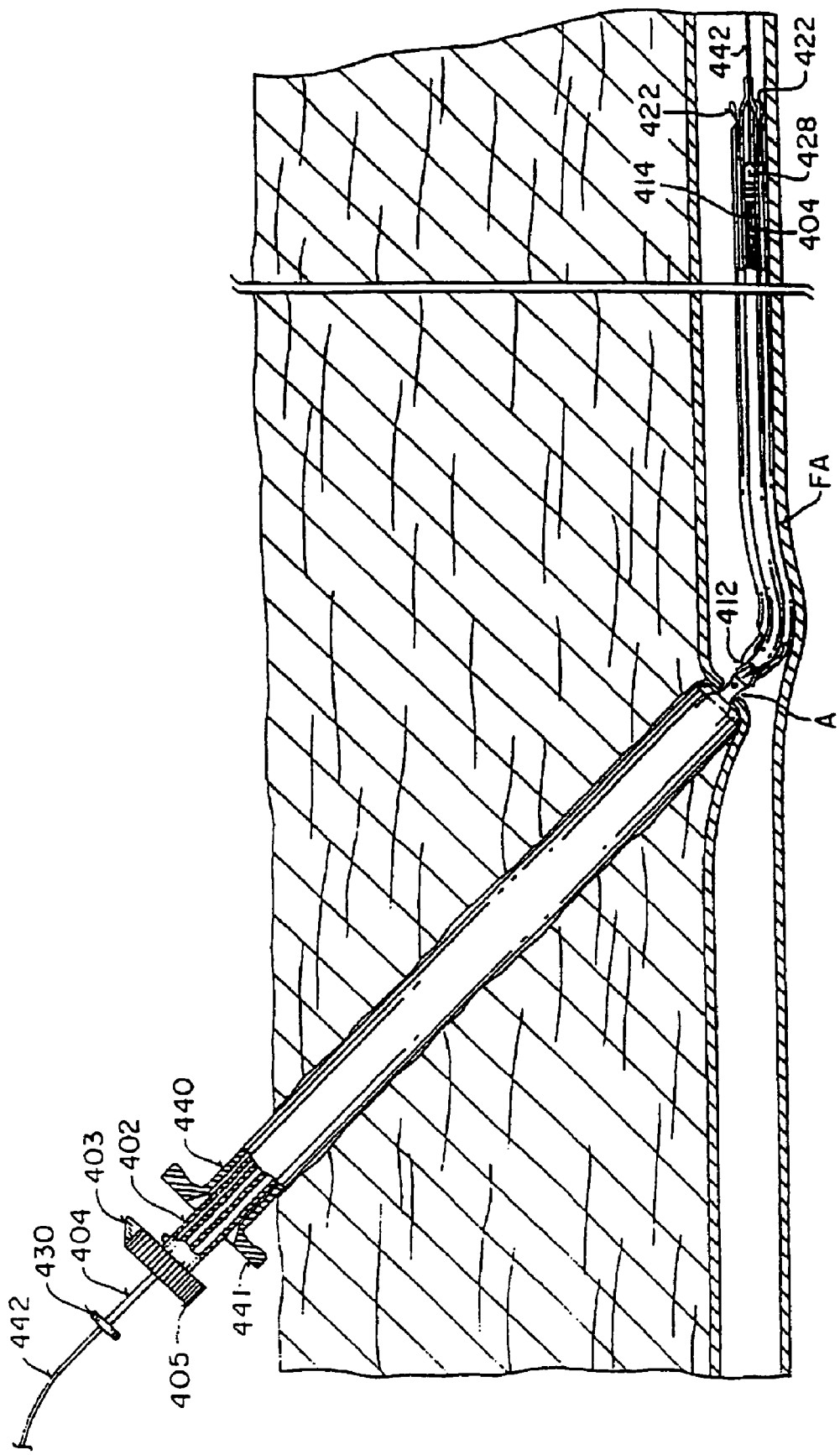
FIGS. 4-7 illustrate the method of the present invention using the suturing device 30 of FIG. 1.
Figure 5:
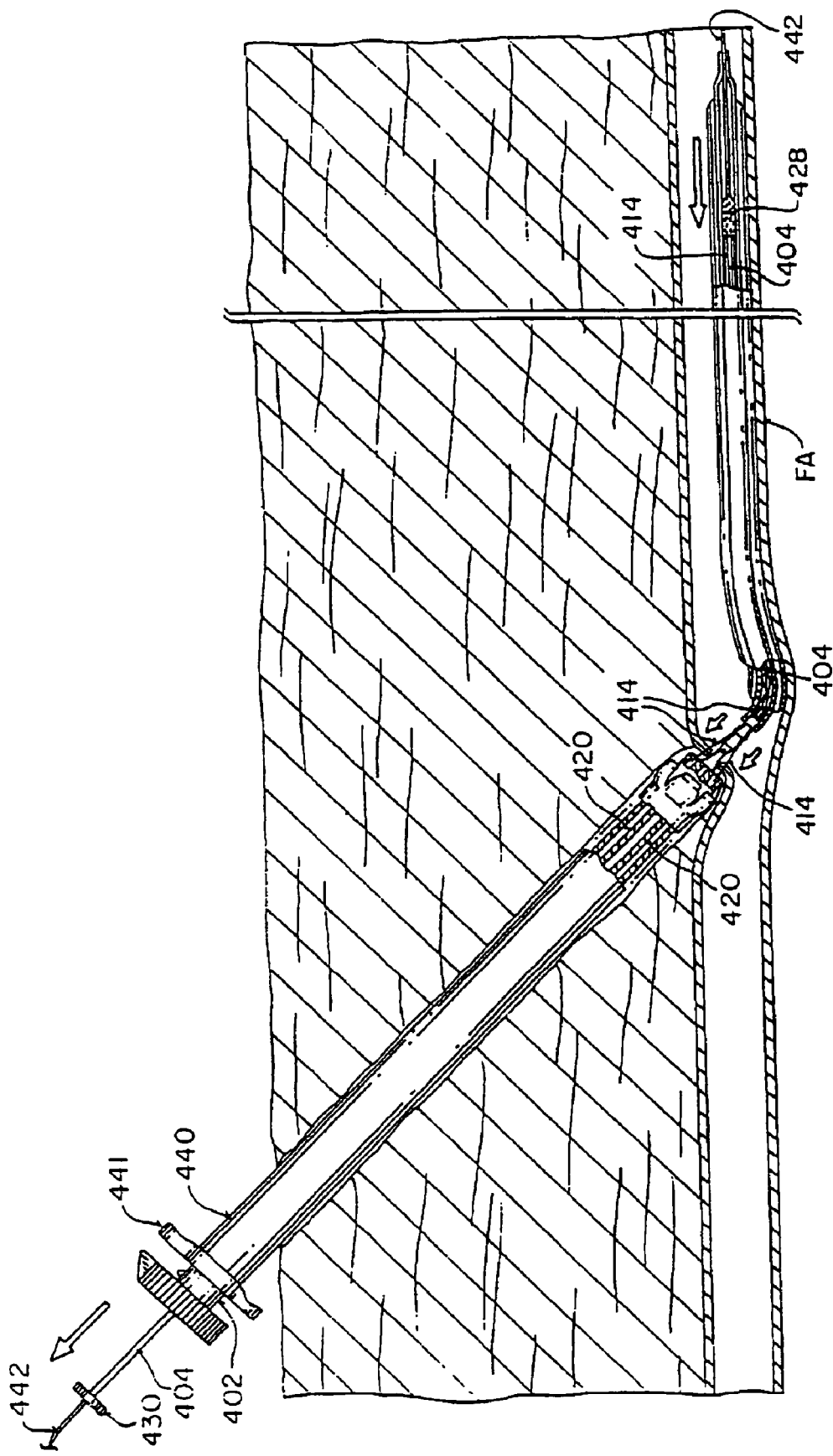
Figure 6:
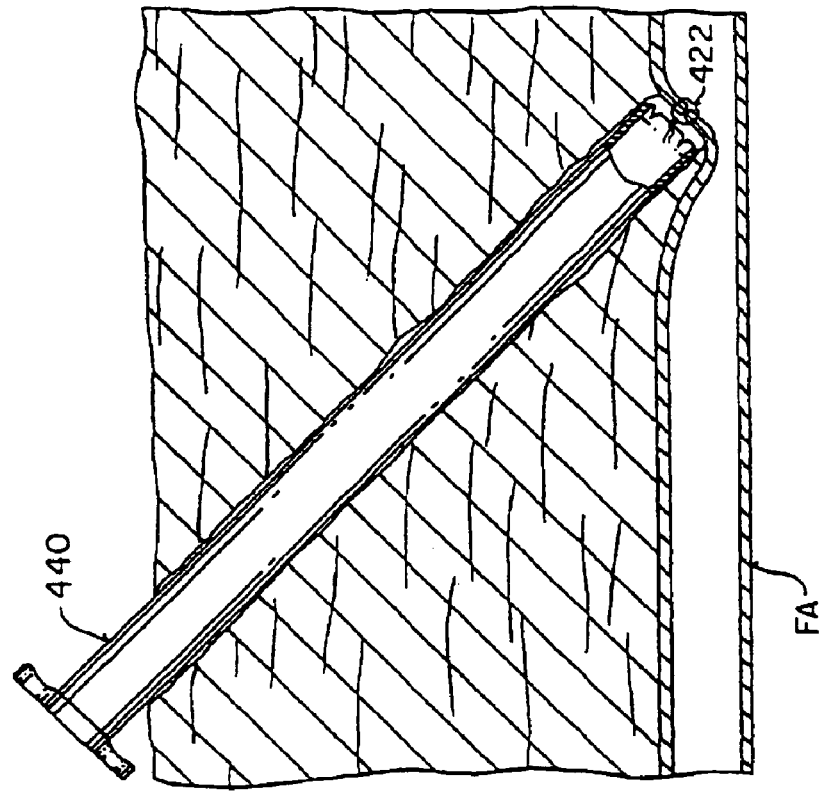
Figure 7:
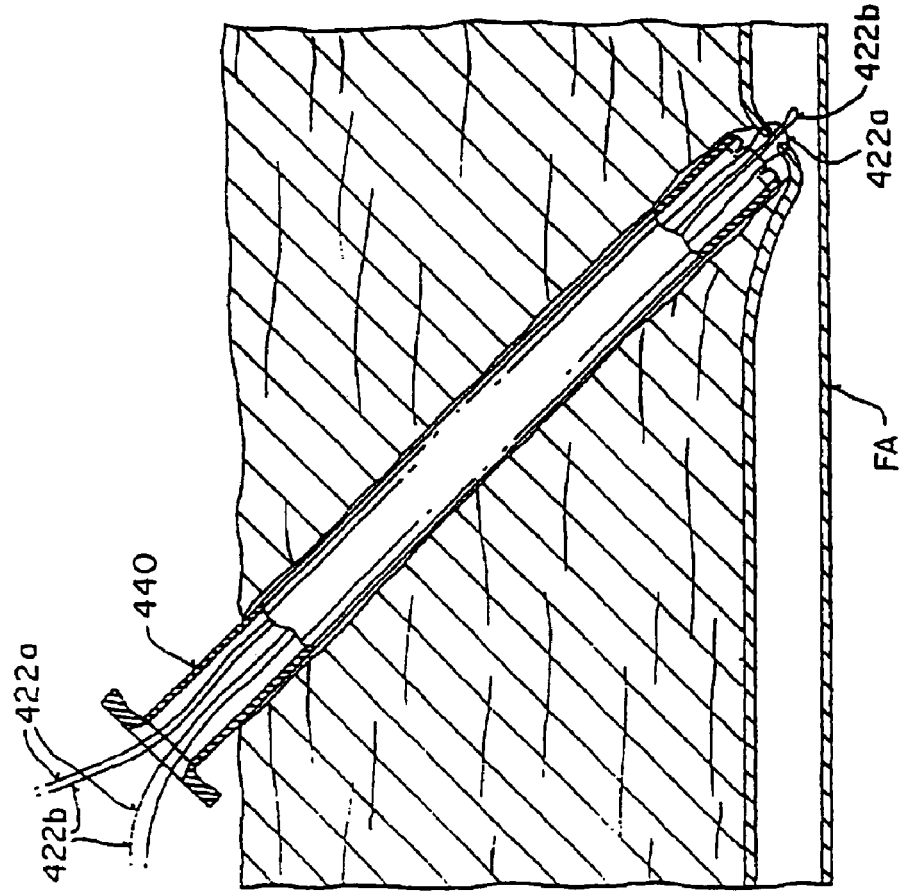

The situation following an interventional or other vascular procedure, where the attending physician is satisfied that the puncture site may be sealed, is illustrated in FIG. 4. A conventional introducer sheath is in place with a guidewire passing into the femoral artery. The conventional introducer sheath is withdrawn after assuring that an appropriate guidewire for the suturing process is in place. The device 400 (including a support sheath 440 which initially covers the ports to the needle lumens 420) will then be introduced over the guidewire, as illustrated in FIG. 4. The needles 410 and sutures 422 mostly encased by flexible needle sheath 426, will be fully advanced into the femoral artery FA past the arterial puncture site A. Handle 441 on support sheath 440 is then partially withdrawn proximally to expose the needle lumens 420 (as shown in FIGS. 2A, 2B, and 5). Handle 430 will then be drawn proximally outward relative to the guide body 402, causing the needles 410 to pass through the superficial wall of the femoral artery FA and into the needle lumens 420, as illustrated in FIGS. 2B and 5. The handle 430 may continue to be drawn proximally (i.e., outward from the patient) in order to continue to pull the needle shaft 404 through the guide body 402. Such movement of the needle shaft 404, in turn, continues to draw the needles 410 outward through the lumens 420 of the guide body 402 until the tips of the needles are exposed. The user may then grasp the needles and continue to draw them out until the suture is available to the user. The guide body 402 may then be withdrawn from the support sheath 440, leaving a portion of the needle sheath 426 still in the puncture site A to maintain hemostasis. The suture can then be tied and the knot pushed back down through the support sheath 440. The knot will then only be tightened when the needle sheath is finally withdrawn from the puncture site A.

Figure 8:
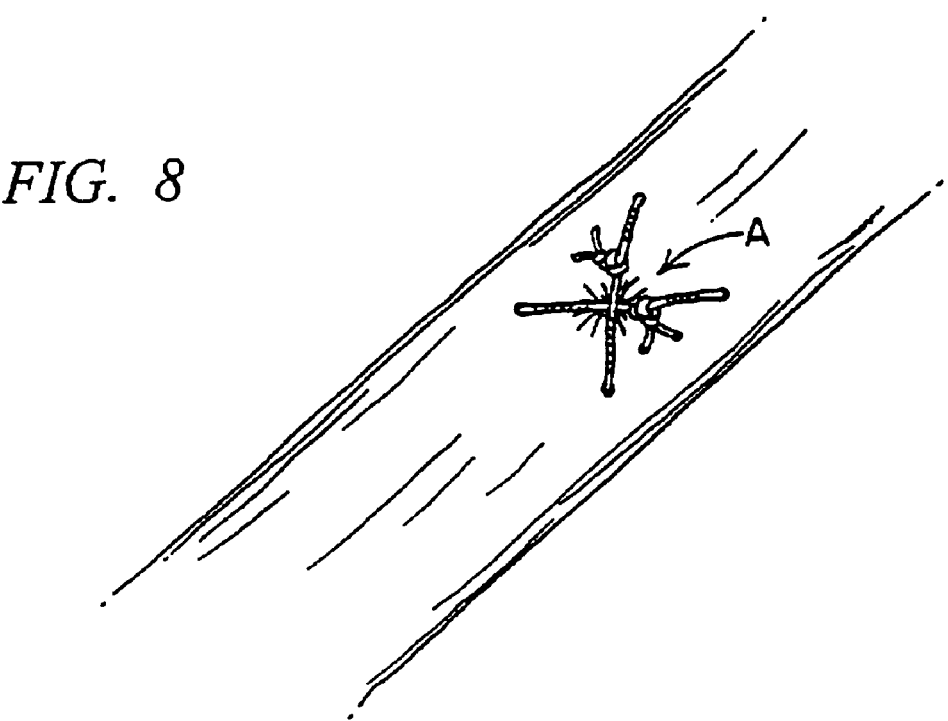
FIG. 8 illustrates the X-pattern of the tied suture applied by the suturing device.

It can be seen that the guide tip 406 deflects the needles radially outward so that the pattern of four needles engages the artery wall in an approximately square pattern about the arteriotomy A. After the sutures are tied and the knots advanced back through the support sheath 440, the resulting pattern of tied suture will appear as in FIG. 8 when viewed towards adventitial surface of the femoral artery FA surrounding the arteriotomy A.

Device 400 has certain advantages over the previous embodiments. Since it is not necessary to capture the needles using an internal capture mechanism, the needles need not have barbs. Such barbless needles will minimize trauma to the arterial tissue around the puncture site A and simplify the procedure. The guide body 402 and guide tip 406 are designed as an integral structure to assure that needles 410 will be precisely centered around the puncture site A, and will very reliably enter the needle lumens 420 in guide body 402. Also, tip 406 will occlude the arteriotomy puncture during the performance of the procedure, providing hemostasis. Moreover, the entire procedure is simplified, with fewer discrete steps being performed. The user need only introduce the device over-the-wire and thereafter draw out the needle shaft to carry the needles through the tissue to be sutured and outward through the guide body, where the suture becomes accessible and may be tied in a conventional manner.

The present invention also provides several devices which comprise a graft anastomosis assembly. One of the preferred embodiments of the graft anastomosis assembly and component devices depicted in the drawings is inserted through an aperture or hole in a tissue wall, such as the wall of the distal artery, an aorta, or other vascular tissue. The assembly mechanically places a predetermined pattern of sutures in the tissue wall. The aperture can then be enlarged manually or, optionally, by the assembly itself, such that the suture pattern is in close proximity to the circumference of the aperture. The assembly provides a graft to the tissue wall at the site of the aperture. Preferably, hemostasis is maintained during a substantial portion of the procedure. Furthermore, the graft anastomosis assembly and devices can maintain perfusion beyond the area of the device introduction through the vascular tissue.

A preferred embodiment of one component for the graft anastomosis assembly is a tissue suturing device 10 shown in FIGS. 9-12 which reliably deploys a uniform suture pattern in a tissue wall 12 defining a blood vessel 14. The tissue suturing device 10 is useable separately for suturing any type of tissue, whether or not as part of an anastomoses procedure. On the other hand, the tissue suturing device 10 can be used to deploy sutures in either, or both, the blood vessel and graft in an anastomosis procedure. Optionally, the tissue suturing device 10 can interlock with a graft suturing device, as will be discussed below, to provide alignment between the suture patterns in the tissue wall 12 and a graft wall.

The tissue suturing device 10 includes an elongated body 16 having a distal end 18 and proximal end 20. Referring specifically to FIG. 9, the tissue suturing device 10 includes a hand grip 22 partially nested within the elongated body 16 and externally accessible to an operator. The device 10 also includes a needle carrier 24, a foot 26 attached to a shaft 28 which extends proximally into the elongated body 16, and an actuating mechanism referred to generally as 30. Supported within the elongated body 16, the actuating mechanism 30 attaches to the hand grip 22 as illustrated by the cut-away portion.

The actuating mechanism 30 includes a cam 32 which is rotatably secured to the elongated body 16 by a fastener 34. The cam 32 is integrally formed with the hand grip 22 and pivots in the directions indicated by arrows 36 using the fastener 34 as the pivot point. The cam 32 includes a slot 38 located between the hand grip 22 and the fastener 34 and extending through the cam itself. The cam 32 slidably connects to the proximal end 40 of the needle carrier 24 by engaging a peg 42 which is affixed to the needle carrier 24 and extends perpendicularly therefrom. Moving the hand grip 22 in the direction of the arrows 36, pivots the cam 32 and slides the peg 42 along the slot 38. As a result, the needle carrier 24 travels along the shaft 28 within the elongated body 16 and reversibly moves the distal end 44 of the needle carrier toward the foot 26.

As specifically illustrated in FIG. 10, the distal end 44 of the needle carrier includes an integrally formed cutting blade 46 mounted on a surface approximating the size of the circumference of the foot 26. One end 48 of the cutting blade is positioned near the shaft 28 so as to meet the circumference of an initial aperture 52 formed in the tissue wall (as shown in FIG. 9). Preferably, the cutting blade end 48 rides in a longitudinal groove 54 (as shown in FIG. 11) formed in the shaft 28 as the distal end 44 of the needle carrier and the foot 26 are squeezed together. The opposite end 50 of the cutting blade is positioned to enlarge the initial aperture 52 in the direction extending away from the shaft 28. The cutting blade 46 preferably has a height profile which decreases from the one end 48 of the cutting blade near the shaft to the opposite end 50 to form a decreasing gradient or slant. The decreasing gradient of the cutting blade 46 allows the end 48 of the cutting blade to first engage and cut the tissue wall 12 near the shaft 28. The cutting blade enlarges the incision toward the opposite end 50 as the distal end 44 of the needle carrier and foot 26 are squeezed progressively together. The present invention also includes embodiments wherein the cutting blade 46 has a uniform height across its length or a gradient which is increasing from the cutting blade end 48 near the shaft to the opposite end 50 of the cutting blade.

Although one embodiment of the cutting blade 46 and the actuating mechanism 30 is illustrated, alternative embodiments are suitable for use with the present invention as may be apparent to one of ordinary skill in the art. A variety of suitable punch/cutting devices, such as circular blades, anvils, and the like, as well as actuating mechanisms, are disclosed in the following prior documents which are hereby incorporated in their entirety by reference thereto: U.S. Pat. Nos. 3,104,666; 3,776,237; 4,018,228; 4,216,776; and 5,192,294 and U.S. Des. Pat. No. 372,310.

The distal end 44 of the needle carrier includes a plurality of needles 56 attached thereto and extending in a generally perpendicular direction. The needles 56 are arranged in a predetermined pattern which matches a desired corresponding suture pattern 58 (as seen in FIG. 12). The needles 56 are positioned at approximately uniform intervals around the circumference of the initial aperture 52 which is enlarged to accommodate a graft (not shown). The height of each of the needles 56 from the surface of the distal end 44 of the needle carrier to its tip is slightly higher than the height of the cutting blade 46 so that the needles 56 engage the tissue wall 12 just as, or slightly before, the cutting blade 46 engages the tissue wall 12. Having the needles 56 engage the tissue wall 12 before, or simultaneously with, the cutting blade 46, allows the tissue wall 12 to be captured and retained in position to form the desired suture pattern 58 even after the cutting blade 46 enlarges the initial aperture 52. The circumference of the enlarged aperture is retained in apposition as the cutting blade 46 completes the incision.

The foot 26 has a top surface 60 and an opposing bottom surface 62 as seen in FIG. 11. The top surface 60 faces the distal end 44 of the needle carrier and has a groove 64 which corresponds in position to the cutting blade 46 on the distal end 44 of the needle carrier. The groove 64 is of sufficient size to accommodate a portion of the cutting blade 46 below the plane of the top surface 60 to facilitate the making of the incision. The groove 64 has the same depth profile from one end 66 of the groove near the shaft 28 to the opposite end 68 as the height profile of the cutting blade 46. Located near the circumference 70 of the top surface 60 is a plurality of suture channels 72 extending through the depth of the foot 26 to the bottom surface 62. The pattern of the suture channels 72 on the top surface 60 corresponds to the pattern of needles 56 on the distal end 44 of the needle carrier (as seen in FIG. 10). As the distal end 44 of the needle carrier travels toward the top surface 60 of the foot, the needles 56 have sufficient height relative to the length of travel by the needle carrier 24 to slightly penetrate the suture channels 72.

Each of the suture channels 72 in the foot are sized to releasably retain a suture 74 having a suture body or length 78 terminating at one end 76. Preferably, the end 76 of the suture is releasably retained in one of the suture channels 72. As illustrated in FIG. 10, a plurality of the sutures lengths 78 extend downward through a lumen 80 in the shaft 28 emerging through a distal shaft aperture 82. As each suture length 78 emerges from the shaft, it is positioned within one of a plurality of suture grooves 84 within the bottom surface 62 of the foot. Each suture groove 84 extends at least partially from the distal shaft aperture 82 to a respective suture channel 72. The depth of each suture groove 84 is sufficient to accommodate the width of the suture length 78 to provide a flush profile to the bottom surface 62. The end of each suture 76 extends to the respective channel 72 where it is releasably retained near the top surface 60 of the foot. Although it is preferred to position the suture end 76 approximately flush with the top surface 60 of the foot, it is suitable for the suture end 76 to be in any position where it can be retrieved or engaged by the corresponding needle 56 or other retrieving device or means when the actuating mechanism 30 squeezes the foot 26 and the distal end 44 of the needle carrier together.

Although a plurality of needles 56 are illustrated on the needle carrier 24 in a one-to-one correspondence with the suture channels 72 on the foot 26, the present invention also provides other embodiments. For example, a single needle or a subset of needles less than the number of suture channels can be used on the needle carrier. The single needle or subset of needles engages a corresponding number of suture channels with a first stroke bringing the foot and needle carrier together. Upon retrieving a corresponding number of sutures, the single needle or needle subset is rotated to a new position after each stroke bringing the foot and needle carrier together along the shaft 28. Rather than having the needles deploy simultaneously with a single stroke, a multi-stroke, successive deployment is used.

Referring to FIG. 9, the suture lengths 78 extend toward the proximal end 20 of the elongated body. The suture lengths 78 exit from the lumen 80 and pass through a longitudinal slot 86 (also illustrated in FIG. 10) which extends along the length of the shaft 28 and the distal end 44 of the needle carrier. Optionally, the suture lengths 78 extend from the longitudinal slot 86 to a guide 88 which organizes the sutures. The guide 88 is located on the external surface of the elongated body near the distal end. The suture lengths 78 extend through a second guide 90 to a suture holder 92. The second guide 90 is located near the proximal end 20 of the elongated body. The suture holder 92 releasably retains the opposite ends 94 of the suture lengths so they may be individually identified as to their position in the suture pattern 58 and retrieved by the operator.

The longitudinal slot 86 allows the removal of the foot 26 from the aperture completed 52 in the tissue wall 12 and the subsequent removal of the suture lengths 78 so that each end, 76 and 94, of the sutures can be fastened together. In an alternate embodiment, the suture lengths 78 extend internally along the length of the elongated body 16 toward the proximal end 20. A seam 98 along the length of the elongated body 16 connects to the end of the longitudinal slot 86 so that the elongated body can be split open to remove the suture lengths 78 once the suture pattern 58 has been completed. The longitudinal slot 86 itself can also be replaced with a seam to similarly split the shaft 28, foot 26, and needle carrier 24 to remove the suture lengths 78 from the lumen 80.

Preferably, the suture pattern 58 is a uniform distance from the perimeter of the completed aperture 52 in the tissue wall. Usually, the initial aperture 52 is a simple longitudinal incision. Preferably, the present invention adjusts for the distance which the tissue wall 12 surrounding the shaft 28 is offset. As illustrated in FIGS. 10 and 11, the foot 26 is partially defined by opposing side walls 100 and end walls which define a heel 102 and toe 104 for the foot. The side walls 100 bulge slightly outward in the vicinity of the shaft 28. Specifically, the distance between the circumference of the shaft and the side walls 100 is the same as the distance from the cutting blade groove 64 or longitudinal axis of the foot 26 to the side walls 100 along the remainder of the foot. Like the remaining suture channels 72, the suture channels in the vicinity of the bulge, like 106 and 108, are located at the circumference of the side walls 100 which offsets suture channels 106, 108 in the suture pattern 58. The offset suture channels 106, 108 provide a uniform amount of tissue wall capture around the entire perimeter of the completed aperture 52 by adjusting the position of the suture pattern 58 for the offset of the tissue wall 12 on each side of the shaft 28. Usually, the tissue wall 12 is negligibly offset by the shaft 28 in the direction of the heel end wall 102 because the shaft is positioned toward or at the heel end wall 102 of the incision creating the initial aperture 52. To further minimize the offset of the tissue wall 12 caused by the shaft 28, it is preferred that the shaft have an oval shape to its cross-section as specifically illustrated in FIG. 11.

The needles 56 on the surface of the distal end 44 of the needle carrier which correspond to the offset suture channels 106, 108 on the foot are similarly offset. The surface of the distal end 44 of the needle carrier in the vicinity of the shaft 28 is offset or bulges in a similar pattern as the opposing side walls 100 of the foot.

FIG. 12 illustrates a side view of the foot 26 upon insertion through the initial aperture 52 in the tissue wall 12. Preferably, the toe end wall 104 is inserted first and moved forward. The shaft has a cut-away portion 110 near its distal end to allow forward movement of the foot assisting the insertion of the heel end wall 102 through the tissue wall 12. The heel end wall 102 is then moved back slightly to abut one end of the initial aperture 52. The top surface 60 of the foot 26 abuts the distal side 112 of the tissue wall promoting uniform tissue capture when the needles engage the top surface 60 of the foot. As the foot 26 passes through the tissue wall 12, the dilated tissue around the aperture 52 usually responds elastically and compresses onto the shaft 28, thereby maintaining hemostasis. Once in position, the top surface 60 of the foot lies adjacent the distal side 112 of the tissue wall, allowing adequate perfusion beneath the bottom surface 62 of the foot and the vessel wall intima 114. When the assembly is used on vascular tissue, the perimeter of the shaft is preferably about equal to the perimeter of the incision. For example, using the tissue suturing device 10 to perform an anastomosis on the distal artery places the diameter of the shaft in a preferred range of about 1.5 mm to about 2 mm which is the generally accepted diameter of the distal artery.

In those operations where the initial aperture 52 is formed by incising the tissue wall 12 or punching a hole of a size approximating the diameter of the shaft 28 in the tissue wall, there is significantly less offset of the tissue wall in the vicinity of the shaft. As a result, a nearly uniform suture pattern 58 is formed without the foot 26 having offset suture channels.

As illustrated in FIG. 13, the present invention includes an embodiment of the foot 26 which does not have an offset or bulge in the side walls 100 in the vicinity of the shaft 28. The same reference numerals are used for like components illustrated in the other figures. FIG. 13 also illustrates the shaft 28 having a more round cross-section shape. The foot 26 can be formed in many other shapes and sizes while employing the inventive concepts described herein to a particular surgical procedure, suture pattern, specific tissue, etc.

As illustrated in FIG. 14A, one preferred embodiment of the foot 26 has a rounded shape to the corners and edges of the top 60 and bottom 62 surfaces to provide for an atraumatic entry through the tissue wall and to guard against traumatizing the tissue wall intima opposite the aperture 52 upon advancing the foot 26 into the lumen of the blood vessel 14 as previously seen in FIG. 12. Another example illustrated in FIG. 14B emphasizes an even more rounded bottom surface 62 than FIG. 14A to guard against traumatizing the vessel wall intima 114 opposite the initial aperture 52.

The foot 26 can also have several cross-sectional configurations as illustrated in FIGS. 14C and 14D for example, which provide a passageway 115 along the longitudinal axis of the foot for perfusion when the foot has been inserted through the tissue wall 12 into a vessel 14 (as seen in FIG. 12). FIG. 14C provides the longitudinal passageway 115 along the length of the foot 26 from the heel end wall 102 to the toe end wall 104. FIG. 14D provides an example of a longitudinal passageway 115 to ensure perfusion being used in combination with a curved top surface 60 to the foot to minimize distortion of the proximal side of the tissue wall 12. A rounded bottom surface 62 prevents traumatizing the vessel wall intima 114 opposite the aperture 52. The suture channels 72 are positioned at an angle to the top surface 60 of the foot so that they are still perpendicular to the needles 56 on a corresponding needle carrier 24 (as seen in FIG. 10).

Other examples of perfusion passageways include pathways which have a baffled or tortuous path. A coiled path is another example of a non-straight perfusion passageway.

Turning now to FIGS. 15-17, the relationship between the sutures 74 and needles 56 is described in more detail. One end 76 of each of the sutures preferably terminates with a cuff 116 attached to the suture length 78 along a bottom exterior wall 118. The cuff 116 has a generally cup-shape interior space 120 defined by a side interior wall 122 and a bottom interior wall 124. The interior space 120 is sized to accommodate one of the needles 56 in a press-fit engagement. The distal end 126 of each needle has an arrowhead shape with a tip 128 and one or more barbs 130. The arrowhead is mounted on a needle shaft 132 which has a tapered section 134 near the arrowhead.

As specifically illustrated by FIGS. 16 and 17, when the needle 56 engages the interior space 120 of the cuff, the diameter of the arrowhead barb 130 is sized to be slightly larger than the interior diameter of the cuff interior space 120. As a result, the cuff side wall 122 deflects slightly as the arrowhead barb 130 is inserted into the interior space. The deflected side wall 122 is biased against the barb 130 to provide a retaining force. The tip 128 of the arrowhead continues until the interior side 124 of the bottom wall is engaged as a backstop to prevent further insertion of the arrowhead tip 128. Penetration of the tip 128 into the interior bottom wall 124 is not required to provide an engaging force between the needle 56 and the suture 74.

For the sake of example, and not to be limited thereby, the preferred dimensions of the needle 56 are in a range of about a 0.01 inch to about a 0.02 inch needle shaft 132 diameter which decreases to a diameter of about 0.005 inch in a tapered section 134. The length of the tapered section 134 at the narrowest diameter is about 0.005 inch with an overall length of about 0.013 inch. The diameter of the arrowhead barb 130 is in the range of about 0.007 to about 0.008 inch. The height of the arrowhead barb 130 is in the range of about 0.010 inch to about 0.014 inch. The height of the interior side of the side wall 122 is about 0.02 inch with the cuff 116 having an overall height of about 0.03 inch. The diameter of the interior space 120 from the interior side of the side wall 122 is about 0.005 inch. The thickness of the side wall 122 is about 0.0025 inch and the bottom wall 118 is about 0.01 inch. The dimensions of each suture channel 72 in the foot 26 for this particular example have an interior diameter at the top surface 60 of the foot of about 0.011 inch.

The suture cuff 116 is preferably welded to the suture length 78 or molded as one-piece from polypropylene. The cuff 116 can be made from other medical polymers or malleable metals with a preferred hardness to provide the retaining force by allowing the arrowhead barb 130 of a needle 56 to deflect and bias the side wall 122 of the cuff against itself and/or allow the barbs 130 of a needle to penetrate the side wall 122 of the cuff.

Other means of attaching the suture length 78 to the cuff 116 are also suitable for use in the present invention such as attaching the cuff to the suture length with a conventional adhesive like cyanoacrylate or by forming the cuff with an indentation in the exterior side 118 of the bottom wall and crimping the suture length therein. In another embodiment, the bottom wall 124 of the cuff can be made of the same, or different, polymer which exhibits a surface hardness sufficient to resist penetration of the tip 128 and provide a backstop preventing excessive penetration. The cuff 116 may also be initially molded as a solid block and subsequently bore an interior space 120 into the solid block to complete the cuff.

Preferably, the suture length 78 is a single strand or monofilament. Although a multi-stranded, covered, twisted, or braided suture length is also suitable for use with the present invention. The cuff 116 is also preferably removable from the suture length 78. A suitable rupture strength of the cuff and suture length attachment is about 2 ounces to about 10 ounces so that the two may be separated with the application of a sharp tug.

The present invention provides other configurations for the suture end 76. Illustrated for the sake of example, and not for limitation, FIGS. 18A-E are suture ends 76 which can be retrieved or fetched by a retrieving device. The suture end 76 in FIG. 18A includes a suture length 78 having a ball-shaped end 136 which is made of a soft material. Similarly, the suture end 76 in FIG. 18B includes a suture length 78 attached to a solid cuff 138 made of a soft material.

The suture end 76 of FIG. 18C includes the suture length 78 attached in a perpendicular manner to one side of a ring 140. Made of deformable material, the ring 140 compresses in the suture channel (not shown) as the larger diameter arrowhead barb is inserted entirely through the hole 142 so that the ring is positioned above the barbs in the tapered section of the needle shaft. As the compressed material relaxes, the ring 140 is retained in the tapered section as the needle is withdrawn through the tissue wall. One end 144 of the ring is preferably tapered to allow for easy passage through the tissue layer. Another example of a retrieving device for use with the ring 140 is a hook as described further below.

The suture end 76 of FIG. 18D includes the suture length 78 attached to a cuff 146 defined by a serrated side-wall 148 providing slits 150 therein. The barbs of the needle previously discussed easily deform the side wall 148 and at least partially fill into one or more of the slits 150 to provide a solid engagement therebetween.

The suture end 76 of FIG. 18E includes the suture length 78 which terminates in a hook-shaped end 152 made of a material sufficiently hard to resist flexing as it is pulled through the tissue layer. Configurations of the suture end like the hook-shaped end 152 can be engaged by a retrieving device like, for example, a similarly shaped hook or by passing the hook-shaped end through the center of a retrieving device having a ring shape.

Other configurations of the retrieving device provided by the present invention are illustrated for example, and not limitation, in FIGS. 19A-E. Preferably, the retrieving device of the present invention generally includes means for forming a port in the tissue layer through which a suture, or other fastener, is retrieved or introduced. The suture or fastener usually remains within the port.

Specifically, another configuration suitable for impaling the suture end is illustrated in FIG. 19A as a serrated needle tip 154 effectively using a plurality of barbs like 156, 158 at various positions and elevations along the shaft 132 of the needle to engage the suture end.

FIG. 19B retrieves the suture length 78 with a multiple piece assembly 160 having the needle shaft 132 with a tapered section 134 near the tip 128. A separate piece of tubing 162 in the tapered section 134 is initially retracted towards the upper portion 164 of the tapered section until the suture length 78 is biased into an indentation 166 in the bottom 168 of the tapered section. As the needle shaft 132 is withdrawn, the tubing 162 slides downward to the bottom 168 of the tapered section and over the suture length 78 to retain it in place. The tubing 162 can further be configured to have an offset 170 at its bottom end to accommodate the thickness of the suture length 78 while simultaneously covering the portion of the suture resting in the indentation 166. Optionally, the needle shaft 132 having the tapered section 134 can be used without the tubing 162.

FIG. 19C shows the suture length 78 retained within an indentation 172 of the otherwise barbless needle shaft 132 with the aid of a suture loop 174 formed in the shape of a noose with a clasp 176. In place of the clasp 176, the noose can also be formed by tying a knot in the suture loop 174.

Another example of a retrieving device is illustrated in FIG. 19D with the needle shaft 132 having a hook-shaped end 178 with a tip 180 suitable for piercing the tissue layer. Optionally, the hook-shaped end 178 can further include an inwardly facing barb 182 for assistance in retaining the suture end within the bight of the hook-shaped end. Examples of a suture end suitable for use with the hook-shaped end 178 are shown in FIGS. 18C and 18E.

FIG. 19E illustrates another retrieving device having a cannula with a lumen or tube 184 with a removable piercing element such as a needle 186 located within the interior of the tube. The needle 186 is initially used to form a port in the tissue layer to atraumatically introduce the tube 184 through the tissue within the proximity of the suture end. The needle 186 is subsequently removed and the interior of the tube 184 is placed under a vacuum sufficient to draw the suture end to the end 188 of the tube. The tube 184 engaged to the suture end is then drawn through the tissue layer. Examples of a suture end suitable for use with the tube 184 are shown in FIGS. 18A and 18B.

The present invention provides other means for engaging a portion of a fastener through a tissue layer from the side opposite means for retaining another portion of the fastener in a stationary position. The present invention provides for using a variety of fasteners to form different types of suture patterns. Other examples of the engaging means for a fastener are illustrated in FIGS. 20 and 21.

In FIG. 20 a first tissue layer 200 and second tissue layer 202 are joined by releasably retaining a first portion of a fastener 204 in a stationary position on one side of the first tissue layer. As previously described, the first portion 204 can be releasably retained in the foot 26 of a tissue suturing device. A second portion of the fastener 206 is releasably retained in the distal end 44 of the needle carrier of the tissue device. The second portion 206 includes a needle tip 208 on a needle shaft 210 for piercing and forming a port 212 in the first and second tissue layers. The second portion 206 also includes a base 214 for abutting the second tissue layer 202 and a barb 216 on the needle shaft for engaging and being retained in an indentation 218 formed in the first fastener portion 204. The first fastener portion 204 includes a face 220 for abutting the first tissue layer 200. As the distal end 44 of the needle carrier is squeezed toward the foot 26, the needle tip 208 engages the indentation 218 and the first and second portions of the fastener 204, 206 are retained together. As a result, the first and second tissue layers 200 and 202 are held in apposition.

FIG. 21 illustrates a tissue lay r 222 and a suture 224 are joined by releasably retaining a first portion of a fastener 204 in a stationary position on one side of the tissue layer 222. As previously described, the first portion 204 can be releasably retained in the foot 26 of a tissue suturing device. A second portion of the fastener 206 is releasably retained in the distal end 44 of the needle carrier of the tissue device. The second portion 206 includes a needle tip 208 on a needle shaft 210 for piercing and forming a port 212 in the tissue layer 222. The second portion 206 also includes a base 214 for abutting the tissue layer 222 and a portion of the suture 224. A barb 216 on the needle shaft passes through an aperture 226 in the first fastener portion 204 and is retained therein. The first fastener portion 204 includes a face 220 for abutting the opposite side of the tissue layer 222. As the distal end 44 of the needle carrier is squeezed toward the foot 26, the needle tip 208 passes through the aperture 226 and the first and second portions of the fastener 204, 206 are retained together. As a result, the first and second portions of the fastener secure the suture 224 therebetween.

The present invention is not limited to retrieving a suture only at its end. As illustrated in FIG. 22, another embodiment of the cuff 116 attaches directly to a suture length 78 and not the terminal end 76 of the suture forming two lengths 230, 232 of the suture extending from the exterior bottom wall 118 of the cuff. Although the cuff 116 can be integrally formed as one-piece with the suture length 78, the cuff can be attached to the suture length with a conventional adhesive. The suture length 78 can be one of a plurality of sutures that are deployed to form the suture pattern.

The suture length-cuff attachment illustrated in FIG. 22 can be used to form a suture pattern 58 in proximity to the aperture 52 in the tissue layer as illustrated in FIGS. 23 and 24 using either a single or a continuous suture. Using suture cuffs 116 periodically attached along the length of a continuous suture 234 as described in FIG. 22, the cuffs 116 are releasably retained in the suture channels 72 of the foot 26 as previously described. The needles 56 penetrate the tissue wall 12 forming a port 236 to engage each cuff 116, and pull each cuff through the tissue wall. Each cuff 116 is removed from the attached two ends 230, 232 of the suture length to form a suture loop 238 which proximally extends through and returns distally through the tissue wall at each port 236. Each suture loop 238 is exposed on the proximal side 240 of the tissue wall can be utilized in several ways such as by attaching one or more separate sutures like 242, fasteners, or anchors on the proximal side 240 of the tissue wall in order to attach a graft (not shown) or to close the aperture 52. For example, a corresponding plurality of separate sutures such as 242 attached at one end to a graft can be passed through each of the exposed suture loops 238. Each separate suture 242 can also accommodate an anchor therethrough so that as the lengths 230 and 232 of the suture are pulled to draw each of the suture loops 238 approximately flush with the proximal side 240 of the tissue wall. The separate sutures 242 can also be tightened to bring the graft in apposition with the proximal side 240 of the tissue wall. The separate sutures 242 can then be tied off.

As illustrated in FIG. 24, a purse-string suture pattern 246 in proximity to the aperture in the tissue layer uses a single suture 248 having free ends 250. To prevent drawing the suture loops 238 completely through the tissue layer, a conventional anchor 244 is positioned underneath each suture loop 238 at each port 236 and pulling the free ends 250 of the suture to draw the pattern closed. This suture pattern 246 would be useful, for example, to close a puncture site or aperture 52.

Another embodiment of the inventive tissue suturing device 310 is shown in FIGS. 25-26. The tissue suturing device 310 includes an elongated body 316 having a distal 318 and proximal 320 end. An actuating mechanism (not shown for clarity) operates a foot 326 in a reversible motion against the distal end 344 of a needle carrier 324 using a shaft 328. The distal end 344 of the needle carrier optionally includes integrally formed cutting blades like 346 on each side of the shaft mounted on a surface approximating the size of the circumference of the foot 326. The distal end 344 of the needle carrier includes a plurality of needles 356 attached thereto and extending in a generally perpendicular direction. The needles 356 are arranged in a predetermined pattern which matches a corresponding suture pattern 358. The needles 356 are positioned at approximately uniform intervals around the circumference of the completed aperture which is being enlarged or slit to accommodate a graft (not shown). The height of each of the needles 356 from the surface of the distal end 344 of the needle carrier to its tip is higher than the thickness of the tissue layer the needles 356 are anticipated to penetrate.

The foot 326 has a top surface 360 facing the distal end 344 of the needle carrier and an opposing bottom surface 362. Located on the top surface 360 is a plurality of suture channels 372 extending at least partially into the depth of the foot. The pattern of the suture channels 372 on the top surface corresponds to the pattern of needles 356 on the distal end 344 of the needle carrier. As the distal end 344 of the needle carrier slides along the shaft 328 towards the foot, the needles 356 on the distal end have sufficient height relative to the length of travel by the needle carrier 324 to penetrate the suture channels 372.

Each of the suture channels 372 in the foot are sized to allow insertion by the tip 380 of the needles. The top surface 360 releasably retains the sutures, preferably loops 382 formed by one or more of the sutures. A plurality of suture lengths 378 extend downward through grooves 384 in the shaft emerging along the top surface 360 of the foot to be positioned within one of a plurality of suture grooves 386 within the top surface of the foot. Each suture groove 386 extends at least partially from the grooves on the shaft to a respective channel 372. The depth of each suture groove 386 is sufficient to accommodate the width of the suture to provide an approximately flush profile to the top surface 360. Each suture length 378 extends to the respective channel 372 where it is releasably retained near the top surface 360 of the foot. Although it is preferred to position the suture length 378 approximately flush with the top surface 360 of the foot, it is suitable for the suture length 378 to be in any position where it can be retrieved by the corresponding needle 356 when the actuating mechanism squeezes the foot 326 and distal end 344 of the needle carrier together.

As specifically shown in FIG. 26, each suture length 378 extends from the groove 386 in the top surface of the foot and forms the suture loop 382 in a stationary position around the respective suture channel 372. The respective needle 356 travels in a perpendicular direction into the suture channel 372. The suture loop is tensioned or biased towards the needle 356, preferably by being positioned to slightly overlap the path of travel expected for the needle 356. As the needle 356 is inserted into the suture channel 372, the suture loop 382 is positioned to engage the side of needle shaft 388 near the needle tip 380. As the needle 356 continues its downward insertion, the suture loop 382 is pushed slightly to one side until the needle 356 has been inserted sufficiently deep for the indentation 390 in the side of the needle shaft 388 to reach the suture loop 382. The tension on the suture loop 382 biases it toward the needle shaft 388 so the suture loop slides into the indentation 390 in the needle shaft given the opportunity for the suture loop to return to its initial position. It is not necessary to move the suture loop 382 toward the needle shaft 388 to engage the indentation 390. Proper position of the suture loop 382 relative to the side of the needle shaft 388 creates the desired bias to have the suture loop return to its starting position when the indentation 390 is adjacent the suture. Subsequently removing the needle 356 from the suture channel 372 back through the tissue layer pulls the suture loop along and passes it through the tissue layer.

Other embodiments of retaining the suture length 378 in the suture channel 372 are shown in FIGS. 27-29. The suture channel 372 in the top surface 360 of the foot retains a button 392 made of deformable material in a press-fit. Alternately or in combination therewith, the button 392 is supported from the inside of the foot by an elastic tube or spring 394 which is positioned between the button and the bottom 362 of the foot.

As specifically shown in FIG. 28, the button 392 has a preferred tear-drop shape so that the suture loop 382 fits between the bottom and the edge of the suture channel 372. The suture loop 382 is tensioned or biased against the button 392 as previously discussed. The button 392 includes an outer surface having an indentation 396 accessible to the needle 356 from the exterior side of the top surface 360 of the foot as seen in FIG. 27. As the needle tip 380 is inserted into the outer surface indentation 396, the button 392 is not depressed by the needle 356 until the indentation 390 or barb of the needle shaft is about even with the outer surface of button to align the suture 382 with the barb or needle indentation 390. As seen in FIG. 29, the needle 356 further depresses the button 392 which releases the suture loop 382 which slides into the barb or needle indentation 390. The needle 356 is withdrawn and pulls the suture loop 382 back through the suture channel 372 and, subsequently, through the tissue layer.

Although the embodiments of the tissue suturing device discussed above show the needles 358 penetrating the tissue layer from a perpendicular direction into a foot having a flat or planar top surface 360, the present invention is not so limited. Another embodiment 510 of the inventive tissue suturing device is shown in FIG. 30. The tissue suturing device 510 includes an elongated body 516 having a distal end. An actuating mechanism (not shown for clarity) operates the foot 526 in a reversible motion against the distal end 544 of a needle carrier using the shaft 528. The distal end 544 of the needle carrier optionally includes integrally formed cutting blades 546. The distal end 544 of the needle carrier includes a plurality of needles 556 attached thereto. The needles 556 are positioned near the circumference of the distal end 544 of the needle carrier and extend downward toward the foot 526 and inward toward the shaft 528 forming an obtuse angle relative to the side surface of the elongated body 516.

The foot 526 has a curved top surface 560 facing the distal end 544 of the needle carrier and a curved opposing bottom surface 562. Located on the top surface 560 is a plurality of suture channels 572 extending at least partially into the depth of the foot 526. The pattern of the suture channels 572 on the top surface 560 corresponds to the pattern of needles on the distal end 544 of the needle carrier. As the distal end 544 of the needle carrier slides along the shaft 528 allowing the foot 526 to travel towards the distal end, the needles 556 on the distal end have sufficient height relative to the length of travel by the foot to penetrate the suture channels.

Each of the channels 572 in the foot are sized to allow insertion by the tip 580 of the needles. A plurality of suture lengths 578 extend downward through grooves 584 in the shaft emerging along the top surface 560 of the foot to be positioned within one of a plurality of suture grooves within the top surface of the foot. Each suture length 578 is positioned where it can be retrieved by the corresponding needle 556 when the actuating mechanism squeezes the foot and distal end of the elongate body together in the manner described above.

Another preferred embodiment of a tissue suturing device 610 is illustrated in FIG. 31. The actuating mechanism 630 includes a motor 682 secured to the elongated body 616. The motor 682 rotatably connects at one end to a worm gear 684 which connects to the proximal end 640 of the needle carrier. The hand grip 622 includes a switch 686 connected to the motor 682 to control the direction and number of revolutions by the worm gear 684. Activating the switch 686 energizes the motor 682 to turn the worm gear 684 and advance the needle carrier 624 along the shaft 628 within the elongated body 616. Once the needle carrier 624 has advanced to retrieve the sutures in the foot 626, the motor 682 is stopped by manually deactivating the switch 686 or by using an automatic cut-off. The switch 686 can then be activated to have the motor 682 turn the worm gear 684 in the opposite direction and reverse the travel of the needle carrier 624 to pass the sutures proximally through the tissue. A power source 688 for the motor 682 is included within the elongated body 616 although an external power source can also be used.

FIG. 31 also illustrates a graft anastomoses assembly 700 which includes a graft suturing device 710 as a second component. A preferred embodiment of the graft suturing device 710 is illustrated in FIGS. 31 and 32. The graft suturing device 710 reliably deploys a uniform graft suture pattern in a graft wall. The graft suturing device 710 is useable separately for suturing any type of graft, whether or not as part of an anastomoses procedure. Optionally, the graft suturing device 710 can interlock with a tissue suturing device like 610 to provide alignment between the suture patterns in the tissue wall and a graft wall The graft suturing device 710 includes a graft needle carrier 724, a graft foot 726 attached to a shaft 728 which extends into the elongated body 616 of the tissue suturing device 610, and the actuating mechanism 630 which can be the same as used by the tissue suturing device 610.

The graft needle carrier 724 includes a distal end 744 having a mounting surface with an integral cutting blade 746 thereon. The cutting blade 746 has a circular shape. The distal end 744 of the needle carrier includes a plurality of graft needles 756 attached thereto and extending in a generally perpendicular direction. The graft needles 756 are arranged in a predetermined pattern which matches a corresponding graft suture pattern 758. The graft needles 756 are positioned at approximately uniform intervals around the circumference of the wall of the graft end 782 (as seen in FIG. 32). The height of each of the graft needles 756 from the surface of the distal end 744 of the graft needle carrier to its tip 780 is slightly higher than the height of the graft cutting blade so that the needles engage the graft wall just as, or slightly before, the edge of the cutting blade 746 engages the wall near the graft end 782. Having the needles 756 engage the wall near the graft end 782 before, or simultaneously with, the cutting blade 746 allows the wall of the graft end 782 to be captured and retained in position to form the desired suture pattern 758 even after the edge of the cutting blade 746 cuts the wall near the graft end 782.

Another suitable embodiment of the cutting blade 746 preferably has a decreasing depth profile forming a decreasing gradient or slant from the one side of the graft needle carrier 724. The decreasing gradient allows the end of the cutting blade edge to engage and cut the graft end 782 in an oblong shape. The edge of the cutting blade makes the cut as the distal end 744 and graft foot 726 are squeezed progressively together. The present invention also includes embodiments wherein the cutting blade 746 has a uniform height across its length. An oblong shape or other desired shape can still be formed with a cutting blade 746 of uniform height by changing the circular shape of the cutting blade on the surface of the distal end 744 to the desired shape.

Referring specifically to FIG. 31, the graft foot 726 has a top surface 760 facing the distal end 744 of the graft needle carrier and an opposing bottom surface. The top surface 760 has a graft groove which corresponds in position to the graft cutting blade on the distal end 744 of the graft needle carrier. The graft groove is of sufficient size to accommodate a portion of the edge of the graft cutting blade below the plane of the top surface to facilitate the making of the cut. Located near the circumference of the top surface is a plurality of suture channels 772 extending through the depth of the graft foot to the bottom surface. The pattern of the suture channels 772 on the top surface corresponds to the pattern of graft needles on the distal end 744 of the graft needle carrier. As the distal end 744 of the graft needle carrier travels toward the top surface of the graft foot, the graft needles 756 have sufficient height relative to the length of travel by the graft needle carrier 724 to penetrate the channels 772.

Each of the suture channels 772 in the graft foot are sized to releasably retain a suture length 778, preferably the end 776 of the suture as previously described. Although it is preferred to position the suture end 776 approximately flush with the top surface of the foot, it is suitable for the suture end to be in any position where it can be retrieved or engaged by the corresponding graft needle 756 or other retrieving device or means when the actuating mechanism squeezes the foot and the needle carrier together. The suture lengths 778 extend within a lumen 780 in the graft shaft 728 to the surface of the distal end 744 of the graft needle carrier where a slot in the cutting blade allows the suture lengths 778 to extend to the external side of the elongated body 616 as previously described with regard to the tissue suturing device 610. The graft shaft 728 extends to connect to the shaft 628 of the tissue suturing device or can be integrally made as a one-piece member.

The actuating mechanism 630 connects to the graft needle carrier 724 in the same manner as between the actuating mechanism and the needle carrier 624 of the tissue suturing device 610 in any of the embodiments previously described. FIG. 31 illustrates one such embodiment wherein the actuating mechanism includes the motor 682 secured to the elongated body. The motor 682 rotatably connects on the opposite end to a second worm gear 784 which connects to the proximal end 740 of the graft needle carrier. The hand grip 622 includes a switch 686 connected to the motor to control the direction and number of revolutions by the worm gear. Activating the switch energizes the motor to turn the worm gear and advance the needle carrier along the shaft within the elongated body. Once the graft needle carrier 724 has advanced to retrieve the suture ends 776 in the foot 726, the motor is stopped by manually deactivating the switch or by using an automatic cut-off. The switch 686 can then be activated to have the motor turn the second worm gear 784 in the opposite direction and reverse the travel of the needle carrier to pass the sutures proximally through the tissue. Although one embodiment of the cutting blade and the actuating mechanism is illustrated, alternative embodiments are suitable for use with the present invention as may be apparent to one of ordinary skill in is the art.

Two other embodiments of a graft suturing devices 810 are shown in FIGS. 33-34 wherein the needles and suture channels are positioned on the opposite components of the device compared to the previously described embodiments. The graft suturing devices 810 integrally mounts the foot 826 on the proximal end 820 of the elongated body 816. A shaft 828 extends from the proximal end 820 of the elongated body 816 to connect to the needle carrier 824 and to an actuating mechanism (not shown). A graft 800 is pulled over the needle carrier 824 and extends toward the foot 826. The foot 826 includes suture channels 872 which releasably retain sutures 874 and are in alignment with needles 856 on the needle carrier. As previously described, the needles 856 move axially to engage the sutures 874 and retrieve the sutures through the graft 800.

Specifically, FIG. 33 ties one end 802 of the graft to the shaft 828 with a tie 804. A cutting blade 846 is located inwardly of the needles 856 toward the shaft 828. As a result, when the foot 826 and needle carrier 824 are drawn together, the sutures 874 will be drawn through the graft 800 from the external wall 806 to the internal wall 808. The sutures 874 can then be pulled out through the open end 802 of the graft once the graft is removed from the needle carrier 824.

In FIG. 34, the graft 800 is positioned over the shaft 828 and pulled through the needles carrier 824. The graft 800 is further positioned over the top surface 860 of the foot to provide the cutting blade 846 with proper alignment to cut the graft in the proximity of the end 802. Since the graft 800 extends through the needle carrier 824, an indexing device 830 provides the proper alignment for the needles 856 to engage the sutures 874 and for the cutting blade 846 to cut the graft end 802. Optionally, the needle carrier 824 may be detachable from the remainder of the graft suturing device 810.

Another embodiment of a graft suturing device 910 is shown in FIGS. 35-37 which includes a graft needle carrier 924, a graft foot 926 attached to a shaft 928. Optionally, the graft shaft 928 may extend into the graft anastomosis assembly. A graft 900 is positioned coaxially about the graft foot 926 and held in position with a tie 909. The graft foot 926 contains suture channels 972 for releasably retaining sutures 974. The sutures 974 extend from the graft foot through suture grooves 984. The suture channels 972 are positioned in an axial position relative to the longitudinal axis along the graft shaft 928. As a result, the needles 956 carried by the needle carrier 924 must also retrieve the sutures 972 in an axial position The needles 956 are deployed radially inwardly through the graft 900 in a regularly spaced pattern of penetration sites or ports in the graft.

FIG. 36 specifically illustrates the details of the graft suturing device that permits an inward radial deployment of the needles 956. The graft suturing device 910 further includes an outer cam 902 which deploys as a sleeve around the needle carrier 924 and needles 956. The cam 902 includes ridges 904 and troughs 906 along a surface 908 of the interior circumference of the cam. The cam 902 is rotated about the longitudinal axis along the graft shaft 928 in either a clockwise or counterclockwise direction as indicated by arrows 988. Each of the needles 956 includes a tail 990 which abuts and slides along the interior surface 908. The rotation of the cam 902 moves each of the needles 956 in either an inward or outward direction as the tail 990 encounters either the ridges 904 or troughs 906 respectively. The needles 956 are driven inwardly through the graft 900 to engage the sutures 974. Then the direction of the needles' movement is reversed and the needles 956 move outwardly from the graft 900 with the sutures 974 in tow. The return of the needles 956 to their initial position is assisted by a spring 992 coiled around the needles shaft. Subsequently, the sutures 974 can be released from the needles 956 and the graft 900 can be removed from the cam 902 and graft foot 926.

As illustrated in FIG. 36, the needles 956 move simultaneously inward. In another embodiment, the needles can move inward successively by changing the position of the ridges 904 and troughs 906 relative to each one another.

Other embodiments of the cam 902 provide means for moving the needles 956 outwardly without using a spring-like member. For example, FIG. 37 illustrates using a rail 994 to which the tail 990 of one of the needles is rotatably secured. As the cam 902 rotates in the direction of the arrows 988 and slides along the rail 994, the needle 956 is moved inward and then is positively moved outward as the cam advanced. In a similar example, the interior surface 908 can include the rail to which the tail 990 of the needle is slidably attached. As the cam 902 is rotated, the tail 990 slides along the rail from trough 906 to ridge 904 and vice versa Since the tail 990 is positively attached to the interior surface 908, the needle moves outward without the assistance of a spring-like member.

Referring to FIG. 31, the graft suturing device 710 and the tissue suturing device 610 can be used solely independent (one without the other) or operating together simultaneously or successively. The inventive tissue suturing device 610 and inventive graft suturing device 710 described herein can also be used solely independent with other devices or methods (conventional or not) to perform the other device's function in anastomosis assembly and method. For example, the graft suturing device 710 described in the related applications can be readily adapted to interlock with the tissue suturing device 610 herein.

Preferably, the graft suturing device can be loaded with the graft prior to the insertion and operation of the tissue suturing device. The two devices are then combined into one assembly to provide proper orientation of the graft to the deployed suture pattern in the vessel wall. This results in a two-stroke method being used wherein one needle passes the suture through the graft and a second needle passes the suture through the vessel wall.

In another embodiment, a one-stroke method can be used with the present invention. For example, using only the vessel suturing device, the needles can first pass the suture through the proximal side of the graft before they are attached to the distal end of the vessel suturing device. Then, as described above, the vessel suturing device is inserted through the vessel wall. The suture can then be passed through the distal side of the vessel wall to complete the loop.

The present invention also provides a tissue suturing device and an anastomosis assembly which inserts a portion of the tissue suturing device from a remote access site other than the site of the tissue suturing or anastomosis. Several embodiments of the tissue suturing and/or graft anastomosis assembly which uses a remote access site are illustrated in FIGS. 38-40.

FIGS. 38 and 40 illustrate a remote access site 1000 in the tissue wall 1012 of a blood vessel 1014. A remote foot 1026 is introduced into the blood vessel 1014 through the remote access site 1000. The remote foot 1026 is attached near its heel end wall 1002 to a guide wire 1004 which is controlled at the other end by an actuating mechanism 1030.

The remote foot 1026 has a top surface 1060 with a groove 1064 thereon for facing the distal end of a needle carrier and corresponding to the position of a cutting blade as discussed herein. Located near the circumference 1070 of the top surface 1060 is a plurality of suture channels 1072 extending into the foot 1026. The pattern of the suture channels 1072 on the top surface 1060 corresponds to the pattern of needles on the distal end of the needle carrier that will be attached to the remote foot 1026 at the site where the suture pattern is desired. Each of the suture channels 1072 in the remote foot are sized to releasably retain a suture 1074 having a suture body or length 1078 terminating at one end 1076. Preferably, the end 1076 of the suture is releasably retained in one of the suture channels 1072.

The sutures lengths 1078 extend across the top surface 1060 of the remote foot and to terminate at the bottom of a plug 1006. The plug 1006 releasably retains the ends 1094 of the sutures 1074 opposite the suture ends 1076 retained in the suture channels 1072 so the suture ends 1094 may be individually identified as to their position in the suture pattern and retrieved by the operator. The plug 1006 is detachable from the remote foot by the actuating mechanism 1030. Once the remote foot 1026 has been guided to the desired cite of the suture pattern, the plug 1006 is released from the remote foot by the actuating mechanism 1030 and driven through the tissue wall 1012 of the blood vessel by a releasable connection to a second wire 1009 associated with the guide wires 1004 as seen in FIG. 39. To assist in making an initial aperture 1052 through the tissue layer 1012 for the plug 1006 to pass through, a dilating blade 1008 is preferably mounted on the top surface of the plug. The suture lengths 1078 have an excess amount of length sufficient to allow the plug 1006 to be pulled free of the blood vessel 1014. The excess amount of length is coiled within the remote foot 1026 beneath the bottom surface of the plug 1006 before the plug is released. After the plug 1006 has passed through the tissue wall 1012, the opposite suture ends 1094 can be released.

With the release of the plug 1006, a depression 1098 corresponding to the shape of the plug is left in the top surface 1060 of the remote foot. This depression is adapted to securely receive the distal end of a shaft of a tissue suturing device (not shown) as previously described herein. The shaft is advanced through the initial aperture 1052 into the depression 1098. Attachment of the shaft of the tissue suturing device to the remote foot 1026 provides proper alignment of the needle carrier and needles of the tissue suturing device with the suture channels 1072 of the remote foot.

Optionally, the plug 1006 can be another embodiment of the graft foot previously discussed herein. Referring to FIG. 39, the plug 1006 includes suture channels 1096 for releasably retaining the opposite suture ends 1094. The suture channels 1096 are illustrated in an axial position relative to the longitudinal axis. The plug 1006 can then be attached to the shaft or other positioning device on a graft suturing device as previously described herein specifically with regard to FIG. 35.

An alternate embodiment of the plug 1006 positions the suture channels 1096 along the longitudinal axis so that suture channels 1072 are flush with the top surface of the plug 1006. With this configuration of suture channels 1072, the plug can be attached to the shaft of a graft suturing device as previously described herein specifically with regard to FIG. 31.

Another embodiment of a tissue suturing device and an anastomosis assembly which inserts a portion of the tissue suturing device from a remote access site other than the site of the tissue suturing or anastomosis is illustrated in FIG. 40. The tissue suturing device 1110 in this embodiment uses a needle carrier 1124, a shaft 1128, and a remote foot 1126 as previously described with regard to the embodiments of the non-remote tissue suturing device. The remote foot 1126, however, is attached to a rigid extension 1102 which connects at the other end to the shaft 1128. Similarly, the needle carrier 1124 is attached to a rigid extension 1104 which connects at the other end to the shaft 1128. The extensions 1102 and 1104 allow the remote foot 1126 to be inserted through the tissue layer 1112 into a blood vessel 1114 at a remote access site 1100. As previously described with regard to the various embodiments of the tissue suturing devices, the needle carrier 1124 has a shape corresponding to the remote foot 1126 so that the needles 1156 are aligned with the suture channels 1172.

The suture channels 1172 releasably retain sutures 1174 at one of the ends 1176 while the suture lengths 1178 extend across the top surface 1160 of the remote foot through suture grooves 1184 near the perimeter of the remote foot. The opposite ends 1194 of the sutures terminate in a plug 1106 which is releasably retained flush with the top surface 1160 of the remote foot. One of the needles like 1157 on the needle carrier is aligned to retrieve the plug 1106 and draw it through the tissue layer 1112. After the plug 1106 has been drawn through the tissue layer 1112, the opposite ends 1194 of the sutures can be freed from the plug.

The tissue suturing device 1110 demonstrates that a suture pattern can be deployed at a deployment site 1108 other than the remote access site. Furthermore, the tissue suturing device 1110 does not need an initial aperture at the suture deployment site 1108 in order to deploy the suture pattern. The alignment between the needles 1156 and the suture channels 1172 is provided by the extensions 1102 and 1104 without a shaft extending through an aperture at the deployment site 1108.

Optionally, a cutting blade 1146 can be mounted on the needle carrier 1124 and is positioned to make an incision at the deployment site 1108 to form an anastomosis site different from the remote access site 1100 and not simply enlarge an initial insertion site. The cutting blade 1146 is preferably aligned with the groove 1164 on the top surface 1160 of the remote foot and avoids contact with the suture lengths 1178. Rather than drawing the plug 1106 through a separate port in the tissue layer 1112, the plug 1106 can be drawn through the incision made by the cutting blade 1146.

With the various inventive embodiments, alternate means of fastening the two ends of the suture body together are suitable. For example and not for limitation, the two ends of the suture body can be simply tied in a knot manually or, optionally, with a knot device as is described in copending application U.S. Ser. No. 08/552,211 filed Nov. 2, 1995.

Even though the suture devices are illustrated herein with regard to vascular tissue, it should be understood that the present invention is riot limited to any particular type of tissue. Generally, the devices of the present invention can be used for suturing all types of tissue in many applications. More specifically, the present invention can close apertures in tissue or bind layers of tissue together such as in anastomoses. For example, and not for limitation, the present invention can be used to close apertures in the septum of the heart such as with a atrial septal defect or a patent foramen ovale. The present invention can deploy sutures around the annulus of a valve for the heart or other organs and around the proximity of a prosthesis.

The present invention can be used in anastomoses to provide a direct or indirect communication between two blood vessels, lymphatics, hollow viscera, or other tubular structures. Although the anastomoses between an aperture in a vessel wall and the end of a graft is specifically illustrated, the present invention can also be used to anastomose tubular structures in other configurations such end-to-end, end-to-side, in continuity, conjoined, or closed-end. Examples of specific applications include the CABG methods described herein using vessels and tubular grafts such as the aorta, veins, the internal mammary artery, or superficial temporal artery. An example of an anastomosis involving an organ instead of a blood vessel is a Roux-en-Y operation which implants the distal end of the divided jejunum with the proximal end into the side of the jejunum at a suitable distance below the first to form a Y-shape pattern.

The suturing devices described herein, particularly the tissue suturing devices, can be used on grafts which do not have an open end. In some instances, the open end of a graft is closed off by a clamp or other closure means. An incision is made in the graft to allow penetration of the foot of the tissue suturing device of the present invention into the side of the graft. The tissue suturing device deploys the desired suture pattern and is withdrawn from the graft. The suture pattern is available for attachment to a corresponding suture pattern or other fastener arrangement. In an anastomoses procedure, the corresponding suture pattern is deployed on the selected vessel.

The present invention can be used with catheter-based surgical techniques wherein one of the elements of the devices described herein is delivered to the suture site through a remote or alternate access location. For example, the vessel suturing device described herein can be introduced to the aorta through the femoral artery to the site where the sutures are deployed. The present invention allows indirect visualization of the desired deployment site via marker ports, crystals or the like.

While particular embodiments of the invention have been herein described in detail, it is to be appreciated that the present invention encompasses variations and combinations thereof, as may be apparent to one of ordinary skill from this disclosure. It is therefore to be understood that within the scope of the appended claims, the invention may be practiced otherwise than as specifically described herein.

What is claimed is:

1. A method for closing an opening in tissue, the method comprising:
    providing a molded cuff on an end of the suture;
    advancing an elongated body having a distal end and a flexible sheath extending from the distal end through the opening; and
    advancing a needle through the tissue adjacent the opening to attach a tip of the needle to an inner space of the molded cuff of the length of suture.

2. The method of claim 1, further comprising partially withdrawing the elongated body leaving a portion of the flexible sheath in the opening to maintain hemostasis.

3. The method of claim 1, wherein the flexible sheath defines a guidewire lumen, and the method further comprises positioning a guidewire through the opening and loading the guidewire into the guidewire lumen to advance the flexible sheath through the opening.

4. A method for closing an opening in tissue, the method comprising: providing a suturing device having a shaft, the shaft having a distal end, the device having a foot at the distal end of the shaft; advancing the foot through the opening; positioning a length of suture on a distal side of the tissue, the suture having an end and a molded cuff on the end of the suture, the cuff releasably retained on the foot; advancing a needle through the tissue adjacent the opening to dispose a tip of the needle into an inner space of the cuff to attach the needle to the length of suture; and withdrawing the needle and the suture through the tissue.

5. The method of claim 4, further comprising providing a flexible sheath on the distal end of the shaft.

6. The method of claim 5, further comprising partially withdrawing the suturing device leaving a portion of the flexible sheath in the opening to maintain hemostasis.

7. The method of claim 5, wherein the flexible sheath defines a guidewire lumen, and the method further comprises positioning a guidewire through the opening and loading the guidewire into the guidewire lumen to advance the suturing device through the opening.

8. The method of claim 4, further comprising tying a knot in the suture to close the opening.

9. A method for closing an opening in tissue, the method comprising:
    inserting a guidewire through the opening in the tissue;
    providing a closing device adapted to penetrate the tissue and permit closing of the opening, the closing device comprising a needle on the closing device and a length of suture having a molded cuff on an end thereof, the molded cuff being releasably retained on the closing device;
    using the guidewire to guide a portion of the closing device to a position substantially adjacent the opening;
    positioning a portion of the suture on a distal side of the tissue;
    penetrating the tissue adjacent the opening with the needle, the needle advancing through the tissue to attach a tip the needle within an inner space of the molded cuff on the end of the length of suture; and
    withdrawing the needle and the suture through the tissue to at least partially close the opening.

10. The method of claim 9, further comprising partially withdrawing the closing device leaving a portion of the flexible sheath in the opening to maintain hemostasis.

11. The method of claim 9, wherein the flexible sheath defines a guidewire lumen, and the method further comprises loading the guidewire into the guidewire lumen to guide a portion of the closing device to a position substantially adjacent the opening.

12. The method of claim 9, wherein positioning the closing device substantially adjacent the opening comprises using a guidewire to guide the closing device.

13. The method of claim 12, further comprising partially withdrawing the closing device leaving a portion of the flexible sheath in the opening to maintain hemostasis.

* * * * *

UNITED STATES PATENT AND TRADEMARK OFFICE
CERTIFICATE OF CORRECTION

PATENT NO. : 7,445,626 B2
APPLICATION NO. : 10/737668
DATED : November 4, 2008
INVENTOR(S) : Chrisina D. Gettman It is certified that error appears in the above-identified patent and that said Letters Patent is hereby corrected as shown below:

Title Page
Item (75) Inventors, change "Las Gatos" to --Los Gatos--
Item (57) ABSTRACT, change "be releasably" to --are provided by releasably--
Item (57) ABSTRACT, change "two sides is" to --two sides are--
Item (57) ABSTRACT, change "wall. the" to --wall. The--
Item (56) References Cited, insert --5,353,974 A   10/1994     Brinkerhoff et al.--

Column 2
Line 65, change "each is" to --each are--

Column 5
Line 26, change "include" to --includes--
Line 45, change "graft suturing devices" to --a graft suturing device--

Column 6
Line 47, remove "30"

Column 8
Line 4, change "anastomoses" to --anastomosis--
Line 62, change "plugging"," to --plugging,"--

Column 9
Line 15, change "fasten r" to --fastener--
Line 24, change "site" to --sites--

Column 11
Line 37, change "anastomoses" to --anastomosis--

Column 18
Line 21, change "lay r" to --layer--

Column 19
Line 5, remove "as"

Column 20
Line 48, change "of button" to --of the button--
Line 49, change "suture 382" to --suture loop 382--
Line 56, change "358" to --356--

CERTIFICATE OF CORRECTION (continued)
U.S. Pat. No. 7,445,626 B2

Column 21
Line 45, change "anastomoses" to --anastomosis--
Lines 51-52, change "anastomoses" to --anastomosis--
Line 55, change "wall" to --wall.--

Column 22
Line 53, remove "780"

Column 23
Line 22, change "mounts" to --mount--
Line 42, change "needles" to --needle--
Line 55, change "924," to --924 and--
Line 64, change "972" to --974--
Line 65, change "position The" to --position. The--

Column 24
Line 33, change "advanced" to --advances--

Column 25
Line 28, change "sutures" to --suture--
Line 29, remove "to"
Line 36, change "cite" to --site--
Line 41, change "wires" to--wire--

Column 27
Line 1, change "riot" to --not--
Line 8, change "a atrial" to --an atrial--
Line 37, change "anastomoses" to --anastomosis--

Signed and Sealed this

Twenty-sixth Day of January, 2010

David J. Kappos
*Director of the United States Patent and Trademark Office*